(12) United States Patent
Julis et al.

(10) Patent No.: US 9,908,826 B2
(45) Date of Patent: Mar. 6, 2018

(54) SYNTHETIC METHOD

(71) Applicant: University Court of the University of St. Andrews, St Andrews (GB)

(72) Inventors: Jennifer Julis, Düsseldorf (DE); Stuart Bartlett, Reading (GB); David John Cole-Hamilton, Fife (GB)

(73) Assignee: University Court of the University of St Andrews, St Andrews (GB)

( * ) Notice: Subject to any disclaimer, the term of this patent is extended or adjusted under 35 U.S.C. 154(b) by 0 days.

(21) Appl. No.: 15/115,591

(22) PCT Filed: Jan. 28, 2015

(86) PCT No.: PCT/GB2015/050189
§ 371 (c)(1),
(2) Date: Jul. 29, 2016

(87) PCT Pub. No.: WO2015/114323
PCT Pub. Date: Aug. 6, 2015

(65) Prior Publication Data
US 2017/0174608 A1   Jun. 22, 2017

(30) Foreign Application Priority Data
Jan. 30, 2014  (GB) .................................. 1401612.5

(51) Int. Cl.
C07C 6/02      (2006.01)
C07C 67/333    (2006.01)
C07C 1/20      (2006.01)
B01J 31/22     (2006.01)
C07C 37/50     (2006.01)
(Continued)

(52) U.S. Cl.
CPC ............. *C07C 6/02* (2013.01); *B01J 31/2265* (2013.01); *B01J 31/2278* (2013.01); *C07C 1/20* (2013.01); *C07C 6/04* (2013.01); *C07C 6/06* (2013.01); *C07C 37/50* (2013.01); *C07C 67/333* (2013.01); *B01J 31/2226* (2013.01); *B01J 2531/821* (2013.01)

(58) Field of Classification Search
None
See application file for complete search history.

(56) References Cited

U.S. PATENT DOCUMENTS 6,159,890 A    12/2000  Nubel et al.

FOREIGN PATENT DOCUMENTS

WO   WO 2001/046096 A1   6/2001
WO   WO 2004/056728 A1   7/2004
WO   WO 2007/010453 A2   1/2007
(Continued)

OTHER PUBLICATIONS

Dragutan, V. et al., Ruthenium Indenylidene complexes, 2005, Planinum Metals Rev., 49, (1), pp. 33-40.*
(Continued)

*Primary Examiner* — Yate' K Cutliff
(74) *Attorney, Agent, or Firm* — Susan T. Evans; Jacqueline F. Mahoney; McDermott Will & Emery LLP

(57) ABSTRACT

The invention relates to a method of alkene metathesis. In the method, at least one monoalkene is subjected to ethenolysis in the presence of a diene. The invention also relates to the use of a diene to promote an ethenolysis reaction conducted on a monoalkene.

31 Claims, 2 Drawing Sheets

(51) Int. Cl.
   C07C 6/06       (2006.01)
   C07C 6/04       (2006.01)

(56) References Cited

FOREIGN PATENT DOCUMENTS

| WO | WO 2008/010961 A2 | 1/2008 |
| WO | WO 2011/056874 A2 | 5/2011 |
| WO | WO 2014/041344 A1 | 3/2014 |

OTHER PUBLICATIONS

Vasapollo, G., et al., Cardanol-based materials as natural precursors for olefin metathesis, 2011, Molecules, vol. 16, pp. 6871-6882).*
Manzini et al., "A Highly Active Cationic Ruthenium Complex for Alkene Isomerisation: A Catalyst for the Synthesis of High Value Molecules", ChemCatChem, vol. 5, No. 10, pp. 2848-2851 (2013).
Mathers et al., "Synthesis and polymerization of renewable 1,3-cyclohexadiene using metathesis, isomerization, and cascade reactions with late-metal catalysts", Macromol. Rapid Commun., vol. 32, No. 17, pp. 1338-1342 (2011).
Mmongoyo et al., "Synthesis of a kairomone and other chemicals from cardanol, a renewable resource", Eur. J. Lipid Sci. Tech., vol. 114, No. 10, pp. 1183-1192 (2012).
Nubel and Hunt, "A convenient catalyst system employing $RuCl_3$ or $RuBr_3$ for metathesis of acyclic olefins", J. Molec. Catal. A: Chem., vol. 145, pp. 323-327 (1999).
Perdriau et al., "Selective conversion of polyenes to monoenes by $RuCl_3$ —catalyzed transfer hydrogenation: The case of cashew nutshell liquid", ChemSusChem, vol. 5, pp. 2427-2434 (2012).
Schwab et al., "Synthesis and applications of $RuCl_3$ (32 CHR')$(PR_3)_2$: The Influence of the alkylidene moiety on metathesis activity", J. Am. Chem. Soc., vol. 118, pp. 100-110 (1996).
Schwab et al., "A series of well-defined metathesis catalysts-synthesis of [$RuCl_2$ (=CHR')$(PR_3)_2$] and its reactions". Angew. Chem., Int. Ed. Engl., vol. 34, Issue: 18, pp. 2039-2041 (1995).
Thomas et al., "Highly selective ruthenium metathesis catalysts for ethenolysis", J. Am. Chem. Soc., vol. 133, No. 19, pp. 7490-7496 (2011).
United Kingdom Intellectual Property Office Search Report From UK Patent Application No. GB1401612.5 dated Aug. 26, 2014, 4 pgs.
Vougioukalakis and Grubbs, "Ruthenium-based heterocyclic carbene-coordinated olefin metathesis catalysts", Chem. Rev., vol. 110, pp. 1746-1787 (2010).
Ashworth et al., "On the relationship between structure and reaction rate in olefin ring-closing metathesis", Chem. Commun. (Camb)., vol. 46 No. 38, pp. 7145-7147 (2010).
Boeda et al., "Phosphabicyclononane-containing ru complexes: efficient pre-catalysts for olefin metathesis reactions", J. Org. Chem., vol. 73, No. 1, pp. 259-263 (2008).
Boeda et al., "Ruthenium-indenylidene complexes: powerful tools for metathesis transformations", Chem. Commun., Issue: 24, pp. 2726-2740 (2008).
Carreira et al., "Anatomy of phobanes. diastereoselective synthesis of the three isomers of n-butylphobane and a comparison of their donor properties", J. Am. Chem. Soc., vol. 131, No. 8, pp. 3078-3092 (2009).
Forman et al., "A convenient system for improving the efficiency of first-generation ruthenium olefin metathesis catalysts", Organometallics, vol. 24, pp. 4528-4542 (2005).
Forman et al., "Metathesis of renewable unsaturated fatty acid esters catalysed by a phoban-indenylidene ruthenium catalyst", J. Organometal. Chem., vol. 691, Issue: 24-25, pp. 5513-5516 (2006).
International Search Report and Written Opinion from PCT Patent Application No. PCT/GB2015/050189 dated Apr. 8, 2015, application now published as International Publication No. WO2015/114323 dated Aug. 6, 2015.

* cited by examiner

SYNTHETIC METHOD

CROSS-REFERENCE TO RELATED APPLICATIONS

This application is a U.S. National Stage of International Patent Application No. PCT/GB2015/050189, filed Jan. 28, 2015, which claims the benefit of priority to GB Patent Application No. 1401612.5 filed Jan. 30, 2014, each of which is hereby incorporated by reference in its entirety.

FIELD

The invention relates to a method of alkene metathesis. In the method, at least one monoalkene is subjected to ethenolysis in the presence of a diene. The invention also relates to the use of a diene to promote an ethenolysis reaction conducted on a monoalkene.

BACKGROUND

Olefin (alkene) metathesis is a very well-known synthetic technique, which allows the exchange of substituents between alkenes by transalkylidenation. In recent years, metathesis reactions have been the study of intense research. Indeed, the 2005 Nobel Prize in Chemistry was awarded jointly to the chemists Yves Chauvin, Robert H. Grubbs and Richard R. Schrock "*for the development of the metathesis method in organic synthesis*".

Such redistribution of carbon-carbon double bonds is catalysed by transition metal-containing catalysts. Although other transition metal-based catalysts can be used for metathesis, such as molybdenum-based catalysts, the most common transition metal used is ruthenium, in the form of alkylidene-containing complexes (so-called alkylidene ruthenium complexes, or catalysts), more typically still alkylidene ruthenium complexes which comprise two (generally) neutral ligands and two additional anionic ligands. For a comprehensive review of such alkylidene ruthenium metathesis catalysts, the reader is referred to Ruthenium-based Heterocyclic Carbene-Coordinated Olefin Metathesis Catalysts (GC Vougioukalakis and RH Grubbs, *Chem. Rev.*, 2010, 110, 1746-1787). In this review, emphasis is, as it typically is in the art, focused on the use of catalysts comprising carbene-containing, in particular, N-heterocyclic carbene-containing (NHC-containing) catalysts, the improved thermal and oxidative stability of such catalysts being believed to be attributable to the decreased lability of such carbenes as compared with phosphine ligands, for example, as well as other ligands coordinating through phosphorus atoms, such as phosphites, phosphinites or phosphonites. Indeed, there has been a discernible move away from metathesis catalysts comprising only phosphines as the neutral ligands in favour of carbenes, in particular N-heterocyclic carbenes.

The earliest well-defined alkylidene- and ruthenium-containing metathesis catalysts comprised two phosphine ligands and are often referred to as "First Generation" catalysts. The archetypal First Generation Grubbs catalyst is 1. Developments in this technology led to 2, the first of the so-called "Second Generation" metathesis catalysts, in which one of the tri(cyclohexyl) phosphine ligands (P(Cy)$_3$ ligands) of 1 has been replaced with an NHC. Sometimes, including herein, catalysts of the type epitomised by 1 and 2, i.e. alkylidene ruthenium catalysts with two discrete neutral ligands are referred to as Grubbs metathesis catalysts, or simply Grubbs catalysts. Still further evolution afforded the so-called Hoveyda-Grubbs catalyst 3 (sometimes known as the Grubbs-Hoveyda catalyst), which was reported in the year 2000. This phosphine-free catalyst comprises a coordinating isopropoxy substituent attached to the aromatic ring of the benzylidene group, which replaces one of the neutral ligands. This catalyst and variants of it have proven popular owing to their improved thermal stability and oxygen- and moisture-tolerance in comparison with 1 and 2.

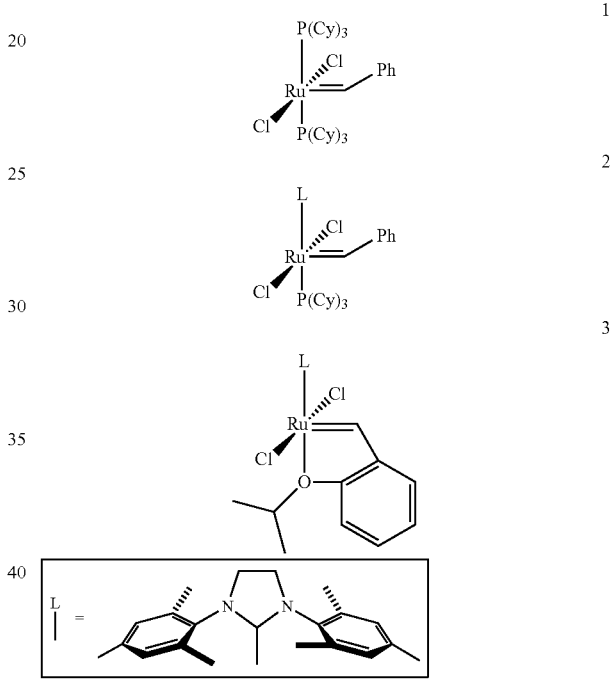

Olefin metathesis reactions may be divided into a variety of subclasses. These include, but are not limited to, so-called cross metathesis, ring-closing metathesis, ring-opening metathesis polymerisation (often referred to as ROMP) and self metathesis reactions.

Cross metathesis appears to be subject to a variety of definitions in the literature, including for example a metathesis reaction between two non-cyclic olefins, and an intermolecular metathesis reaction between terminal alkenes. However, cross metathesis as defined herein is any metathesis reaction between two alkenes. Typically the two alkenes participating in a cross metathesis will be acyclic. It will be understood that, where the participating alkenes are the same, such a cross metathesis reaction is an example of self metathesis. Typically, however, cross metatheses are not self metathetic.

Ring-closing metathesis is a reaction whereby a ring is formed as a result of a metathesis reaction between two carbon-carbon double bonds. For example, an acyclic diene, typically in which the two participating C=C bonds are terminal may be ring-closed. In contrast, ring-opening metathesis polymerisation involves, as the name implies, both ring-opening of a cycloalkene and polymerisation of the resultant diene.

Each of these (and other) classes of metathesis reactions are well-known to and understood by the skilled person and, as discussed above, may be and often are catalysed by alkylidene ruthenium complexes.

G S Forman et al. (Organometallics, 2005, 24, 4528-4542) report enhancement to the performance of certain olefin metathesis reactions catalysed by Grubbs catalysts by the simple addition of phenol or a substituted phenol. In a published patent application (WO 2004/056728 A1), similar metathesis reactions are described. In neither of these publications, however, is it in any way described or contemplated that the substituted phenol may be tethered to a C=C bond participating in a metathesis reaction, in other words that a phenol-comprising molecule participates in a metathesis reaction.

J A Mmongoyo et al. (*Eur. J. Lipid Sci. Technol.*, 114, 1183-1192 (2012)) describe a specific example of a cross metathesis reaction between ethylene and cardanol. Cardanol is a term used to refer to a mixture of compounds each of which is a phenol having a $C_{15}$ hydrocarbyl straight chain at the 3-position and which vary in the degree of internal unsaturation in the chain, which has between 0 and 3 carbon-carbon double bonds. The cross metathesis reaction described is catalysed by the Hoveyda-Grubbs catalyst (3, supra) is described as providing a less than perfect yield, with the reaction giving undesired quantities of other products believed to result from a series of side or competing reactions.

The type of scissile cross metathesis reaction described by J A Mmongoyo et al. Is sometimes referred to as ethenolysis, since the metathesis reaction between ethylene and an internal double bond serves to cleave the internal C=C bond.

In a recent study (R. M. Thomas, B. K. Keitz, T. M. Champagne and R. H. Grubbs, *J. Am. Chem. Soc.*, 2011, 133, 7490-96), Grubbs-Hoveyda-type catalysts containing unsymmetrical N-heterocyclic carbenes are described in which one N substituent is alkyl and the other aryl. These are described as highly selective catalysts for the ethenolysis of methy oleate, the best having di(2-propyl)phenyl and norbornyl substituents.

As is known (see for example the discussion by Thomas et al. (immediately supra), and the references cited therein), ethenolyses are particularly challenging metathesis reactions to conduct. This is believed to be because the catalytic cycle involves reaction between a methylidene complex and the internal alkene being subjected to ethenolysis. Many alkene metathesis catalysts are understood to be unstable as methylidene complexes and it is degradation of these intermediate species that is believed to give rise to the difficulties encountered with ethenolysis reactions.

There is a continual need for modifications and/or improvements to existing ethenolysis methodologies and the present invention addresses this need in the art.

SUMMARY

The present invention arises, in part, from the surprising finding that there is advantageousness to conducting ethenolysis reactions in the presence of dienes. In particular, we have found that the presence of dienes is of benefit to achieving good activity and/or selectivity in ethenolysis reactions.

Viewed from a first aspect, therefore, the invention provides a method of ethenolysis of a monoalkene, comprising introducing into a reaction vessel a monoalkene and a diene, and subjecting the monoalkene to ethenolysis in the presence of a metathesis catalyst and the diene.

Viewed from a second aspect, the invention provides the use of a diene to promote an ethenolysis reaction conducted on a monoalkene.

Viewed from a third aspect, the invention provides an alkene obtained or obtainable by a method of the first aspect of the invention or according to the use of the second aspect of the invention.

Further aspects and embodiments of the present invention will become apparent from the detailed discussion of the invention that follows below.

DETAILED DESCRIPTION

Figure 1:
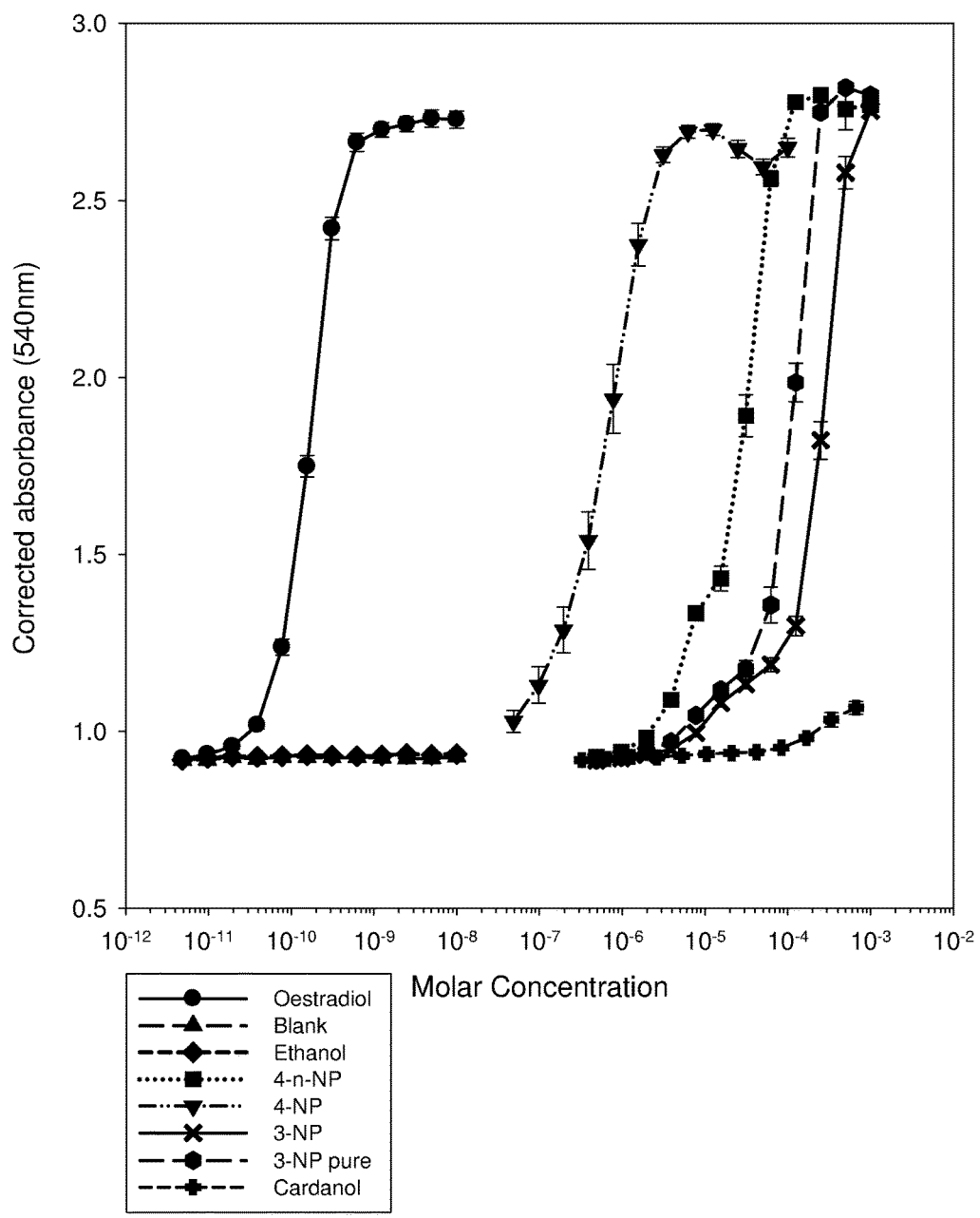
FIG. 1 shows oestrogen response curves for a variety of substrates obtained using a yeast oestrogen screen (YES) assay (4-NP=4-nonylphenol with mixed $C_9$ chains; 4-n-NP=4-nonylphenol with a linear chain; 3-NP=3-nonylphenol prepared in this study by hydrogenation of 3-nonenylphenol, cardanol and crude cashew nut shell liquid).

As noted above, the present invention relates to ethenolysis reactions catalysed by transition metal-containing metathesis catalysts. Whilst there is no particular limitation to the nature of the metathesis catalysts may be used in accordance with the present invention, the most common transition metal used in the metathesis catalysts is ruthenium, particularly in the form of alkylidene-containing complexes (so-called alkylidene ruthenium complexes or catalysts). Accordingly, the present invention focuses on such metathesis catalysts, although the invention is not to be considered to be so limited unless the context specifically indicates to the contrary. By this is meant that, where the discussion refers to alkylidene ruthenium catalysts or complexes, its content may be extrapolated as appropriate to other metathesis catalysts, e.g. molybdenum-based catalysts.

Generally, alkylidene ruthenium complexes, which may be used in accordance with the various aspects of the present invention, comprise two (generally) neutral ligands and two additional anionic ligands. The skilled person is well acquainted with such metathesis catalysts (see the review article by Vougioukalakis and Grubbs (supra).

According to still more particular alkylidene ruthenium complexes useful according to this invention, the invention makes use of a specific subclass of Grubbs catalyst, namely those comprising two phosphine, phosphite, phosphinite or phosphonate ligands. In particular, such catalysts may be defined as alkylidene ruthenium alkene metathesis catalysts comprising two ligands $P^1$ and $P^2$, which may be the same or different and of formula $P(R^1)_3$, in which P is a phosphorus atom coordinated to the ruthenium ion and each $R^1$ is independently an optionally substituted alkyl or alkoxy group; or two $R^1$ groups within one $P^1$ or $P^2$ ligand constitute an optionally substituted bicycloalkyl.

According to particular embodiments of the invention involving use of the ruthenium alkene metathesis catalysts comprising two ligands $P^1$ and $P^2$ described in the immediately preceding paragraph, $P^1$ and $P^2$ are each independently of formula $P(R^1)_3$, in which P is a phosphorus atom coordinating to the ruthenium ion and each $R^1$ is independently an optionally substituted alkyl, alkoxy, aryl or aryloxy group; or two $R^1$ groups within one $P^1$ or $P^2$ ligand of formula $P(R^1)_3$ constitutes an optionally substituted bicycloalkyl.

According to the invention, alkylidene ruthenium catalysts are used to catalyse ethenolysis reactions. The expression "used to catalyse" herein indicates that that the catalyst may be used to promote an ethenolysis reaction in a substoichiometric amount (relative to the monoalkene undergoing metathesis, i.e. ethenolysis), i.e. less than 1 molar equivalent (100 mol %) relative to at least the monoalkene.

The expression "used to catalyse" does not require that the alkylidene ruthenium catalysts with which the monoalkene is contacted is the actual catalytic species since, without wishing to be bound by theory, the alkylidene group in such catalysts is believed to be lost in the first catalytic cycle and the actual catalytic species may be formed in situ by alkylidene exchange with a double bond. Typical substoichiometric amounts will be in the range of about 0.0000001 to about 0.2 molar equivalents, e.g. about 0.00001 to about 0.2 molar equivalents, typically about 0.0001 to about 0.02 molar equivalents, relative to the amount of the monoalkene.

Generally, the alkylidene ruthenium catalysts used according to the invention will be of formula (I):

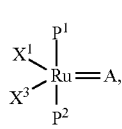

(I)

wherein:

$P^1$ and $P^2$ are as herein defined;

$X^1$ and $X^2$ are anionic ligands, which may be the same or different; and

A is an alkylidene group.

Typically the alkylidene ruthenium catalysts used comprise ruthenium ions, generally in oxidation state +2. It will be understood that these are may be formed in situ or ex situ.

Unless the context specifically suggests otherwise, the term "halide" refers to fluoride, chloride, bromide or iodide, typically chloride, bromide or iodide.

The term aromatic used herein embraces within its scope heteroaromatic. As known to those skilled in the art, and used herein, heteroaromatic moieties may be regarded a subset of aromatic moieties that comprise one or more heteroatoms, typically O, N or S, in place of one or more ring carbon atoms and any hydrogen atoms attached thereto. Such exemplary heteroaromatic moieties, for example, include pyridine, furan, pyrrole and pyrimidine.

Aromatic moieties may be polycyclic, i.e. comprising two or more fused aromatic (including heteroaromatic) rings. Naphthalene and anthracene are examples of polycyclic aromatic moieties, and benzimidazole is an example of a polycyclic heteroaromatic moiety.

Unless the context herein specifically suggests otherwise, aromatic moieties, including aryl and arylene radicals and diradicals (formed formally by abstraction of one or two hydrogen atoms from an aromatic moiety) may be optionally substituted with one or more substituents selected from halo (e.g. fluoro, chloro, bromo and iodo), alkyl, aryl (including heteroaryl), hydroxy, nitro, amino, alkoxy, alkylthio, cyano, thio, formyl, ester, acyl, thioacyl, amido, carbamido and sulfonamide. According to particular embodiments, aromatic moieties herein are typically unsubstituted.

Unless the context herein specifically suggests otherwise, by alkyl is meant herein a saturated hydrocarbyl moiety, which may be straight-chain, cyclic or branched. By alkylene is meant an alkyl group from which a hydrogen atom has been formally abstracted. Typically alkyl and alkylene groups will comprise from 1 to 25 carbon atoms, more usually 1 to 10 carbon atoms, more usually still 1 to 6 carbon atoms. Alkyl and alkylene groups may be substituted, for example once, twice, or three times, e.g. once, i.e. formally replacing one or more hydrogen atoms of the group. Examples of such substituents are halo (e.g. fluoro, chloro, bromo and iodo), aryl, heteroaryl, hydroxy, nitro, amino, alkoxy, alkylthio, cyano, thio, formyl, ester, acyl, thioacyl, amido, carbamido, sulfonamido and the like. Examples of aryl (e.g. heteroaryl) substituted alkyl (i.e. aralkyl (e.g. heteroaralkyl)) include $CH_2$-aryl (e.g. benzyl) and $CH_2$-heteroaryl.

By alkene is meant a compound comprising one or more non-aromatic carbon-carbon double bonds.

By alkyne is meant a compound comprising one or more carbon-carbon triple bonds.

By carboxy is meant herein the functional group $CO_2H$, which may be in deprotonated form ($CO_2^-$).

By acyl and thioacyl are meant the functional groups of formulae —C(O)-alkyl or —C(S)-alkyl respectively, where alkyl is as defined hereinbefore.

By amido is meant a functional group comprising the moiety —N(H)C(=O)—;

By carbamido is meant a functional group comprising the moiety —N(H)C(=O)N(H)—;

By ester is meant a functional group comprising the moiety —OC(=O)—;

By sulfonamido is meant a functional group comprising the moiety —$SO_2$NH— in which the hydrogen atom depicted may be replaced with alkyl or aryl.

Alkyloxy (synonymous with alkoxy) and alkylthio moieties are of the formulae —O-alkyl and —S-alkyl respectively, where alkyl is as defined hereinbefore.

Aryloxy and arylthio moieties are of the formulae —O-aryl and —S-aryl respectively, where aryl is as defined hereinbefore.

Alkylamino and dialkylamino moieties are of the formulae —N(H)-alkyl and

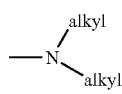

respectively, where alkyl is as defined hereinbefore.

By amino group is meant herein a group of the formula —N(R$^x$)$_2$ in which each R$^x$ is independently hydrogen, alkyl or aryl, e.g. an unsaturated, unsubstituted C$_{1-6}$ hydrocarbyl, e.g. alkyl such as methyl or ethyl, or in which the two R$^x$s attached to the nitrogen atom N are connected. One example of this is whereby —R$^x$—R$^x$— forms an alkylene diradical, derived formally from an alkane from which two hydrogen atoms have been abstracted, typically from terminal carbon atoms, whereby to form a ring together with the nitrogen atom of the amine. As is known the diradical in cyclic amines need not necessarily be purely hydrocarbyl (the alkylene chain —R$^x$—R$^x$— may be interrupted by, for example, one or more heteroatoms (e.g. O, S or NR, wherein R is hydrogen, alkyl or aryl), or indeed saturated: morpholine (in which —R$^x$—R$^x$— is —(CH$_2$)$_2$O(CH$_2$)$_2$—) is one such example of a cyclic amino in which an alkylene chain is interrupted by oxygen.

References to amino herein are also to be understood as embracing within their ambit quaternised or protonated derivatives of the amines resultant from compounds comprising such amino groups. Examples of the latter may be understood to be salts such as hydrochloride salts.

The alkylidene ruthenium catalysts of use according to the present invention typically comprise two anionic ligands (X$^1$ and X$^2$ in formula (I)). These anionic ligands are not particularly limited. Examples include those described in section 7 of GC Vougioukalakis and RH Grubbs (supra). For example, in addition to the often-used halides, anionic ligands may be alkyl or aryl carboxylates or sulfonates, alkoxides or aryloxides optionally in which one or more hydrogen atoms within the alkyl or aryl moieties of such ligands have been substituted with halogen atoms, notably fluorine, for example in which the alkyl or aryl moieties of such ligands have been perfluorinated (by which is meant that all of the hydrogen atoms of hydrocarbyl group R are replaced with fluorine). Specific examples of such anionic ligands include acetate, monofluoroacetate, difluoroacetate, trifluoroacetate, propionate, perfluoropropionate, C$_{1-6}$alkoxides such as methoxide, ethoxide and tert-butoxide, phenoxide, perfluorophenoxide, tosylate, mesylate and triflate. In many embodiments, X$^1$ and X$^2$ will be the same. In many embodiments, X$^1$ and X$^2$ will be halide, typically but not necessarily chloride; bromide and iodide may also be used. In particular embodiments X$^1$ and X$^2$ are each chloride.

Ligands P$^1$ and P$^2$ are each independently of formula P(R$^1$)$_3$. Whilst these ligands may be the same or different, typically they are the same.

Either or both of P$^1$ and P$^2$ may be a phosphine, phosphite, phosphinite or phosphonite. In accordance with the skilled person's understanding of these four classes of phosphorus-containing compound, the terms have their normal meanings: phosphine used herein defines a compound of formula P(R$^1$)$_3$, in which each R$^1$ is independently optionally substituted alkyl; or two R$^1$ groups within one P$^1$ or P$^2$ ligand of formula P(R$^1$)$_3$ constitutes an optionally substituted bicycloalkyl; the term phosphite used herein defines a compound of formula P(R$^1$)$_3$, in which each R$^1$ is independently optionally substituted alkoxy; the term phosphonite used herein defines a compound of formula P(R$^1$)$_3$, in which one R$^1$ group is optionally substituted alkyl and two R$^1$ groups are independently optionally substituted alkoxy; and the term phosphinite defines a compound of formula P(R$^1$)$_3$, in which two R$^1$ groups are independently optionally substituted alkyl or together constitute an optionally substituted bicycloalkyl and one R$^1$ is independently optionally substituted alkoxy.

Typically, although not necessarily, each P$^1$ and P$^2$ is a phosphine or phosphite, for example each P$^1$ and P$^2$ is a phosphine. In each of these embodiments, (i.e. wherein P$^1$ and P$^2$ is a phosphine, phosphite, phosphinite or phosphonite; phosphine or phosphite; or a phosphine), P$^1$ is typically the same as P$^2$.

Typically, although not necessarily, each of the discrete R$^1$ groups within the P$^1$ and P$^2$ ligands comprise from 1 to 20 carbon atoms. The term "discrete R$^1$ groups" is intended to exclude the possibility for two R$^1$ groups together constituting an optionally substituted bicycloalkyl, which optionally substituted bicycloalkyl typically comprises from 8 to 12 carbon atoms. More commonly, at least two of the discrete R$^1$ groups comprise between 5 and 10 carbon atoms, for example all of the discrete R$^1$ groups comprise between 5 and 10 carbon atoms.

The skilled person is very familiar with P$^1$ and P$^2$ ligands suitable for use in alkylidene ruthenium metathesis catalysts. In particular, it is often advantageous for at least two R$^1$ groups to be or comprise a branched alkyl or cycloalkyl group. According to particular embodiments of the invention, P$^1$ and P$^2$ are tricycloalkylphosphines and tricycloalkylphosphites, in particular tricyclopentylphosphine, tricyclopentylphosphite, tricyclohexylphosphine and tricyclohexyphosphite. According to many embodiments of the invention, at least one P(R$^1$)$_3$ group is, and typically both P(R$^1$)$_3$ groups are, tricyclohexylphosphine. Notwithstanding this, however, the skilled person is well aware of the suitability of many other phosphorus-coordinating ligands suitable for use with alkylidene ruthenium metathesis catalysts. For example, reference may be made to tri(tert-butyl)phosphine and tri(iso-propyl)phosphine.

Whilst attention is focused in the present discussion on the use of alkyl-based P$^1$ and P$^2$ groups, the invention is not to be understand to be so limited, the discussion here of such embodiments of the invention also applying mutatis mutandis to other embodiments of the present invention in which one or more R$^1$ groups of ligand P$^1$ and/or P$^2$ may be aryl or aryloxy.

With regard to the possibility of two R$^1$ groups within one ligand of formula P(R$^1$)$_3$ group constituting a bicycloalkyl group, the skilled person will be aware of the description in the art of the use of so-called phobanes—9-phosphabicyclononanes—in metathesis catalysis. In this regard, reference is made to F Boeda et al. (*J. Org. Chem.*, 2008, 73(1), 259-263), M Carreira et al. (*J. Am. Chem. Soc.*, 2009, 131(8), 3078-3092), G S Forman et al. (*J. Organomet. Chem.*, 2006, 691, 5513-5516) and WO 2007/010453 A2 (Sasol Technology (UK) Limited) and the technology described therein. According to particular embodiments of the invention one or both $P(R^1)_3$ groups may be a phobane. In these and other $P^1$ and $P^2$ ligands, the phosphorus atoms are in particular embodiments additionally attached to an alkyl, e.g. cycloalkyl group, for example one comprising between 4 and 20 carbon atoms (e.g. tert-butyl, sec-butyl, cyclohexyl or eicosyl). Phobane-containing metathesis catalysts are available commercially, e.g. from Cytec or Umicore.

In many embodiments of the invention, the $R^1$ groups within $P^1$ and $P^2$ are unsubstituted. Where an $R^1$ group is substituted, however (including embodiments in which two $R^1$ groups within one ligand of formula $P(R^1)_3$ is a substituted bicycloalkyl group), such $R^1$ groups may comprise one or more substituents with which alkyl groups may generally be substituted (vide supra). Notwithstanding this, an $R^1$ group may according to particular embodiments comprise one or more halo substituents; a sulfonate ($—SO_3^-$), phosphate ($—OPO_3^{2-}$) or carboxylate ($—CO_2^-$) group; a quaternary ammonium group; or a poly(ethylene glycol)-containing (PEG-containing) substituent.

Where the substituent of a $R^1$ group is halo, this may be, although not necessarily is, fluoro. Moreover, in particular embodiments, multiple fluoro substitution may be effected, so as to provide perfluorinated $R^1$ groups, or $R^1$ groups comprising perfluorinated portions. As an example of the latter, reference is made to compound 421 in Vougioukalakis and RH Grubbs (supra), and the references cited therein. Compound 421 comprises a partially perfluorinated trialkyl phosphine in which each of the groups of the phosphine is a perfluorodecylethyl moiety. As is described, such fluorine substitution can be advantageous in effecting metathesis reactions in both monophasic and biphasic solvent mixtures (for example in dichloromethane and dichloromethane/fluorine-containing solvent mixtures) with improved reaction rates found when conducting metathesis reactions in such biphasic solvent mixtures.

Where a substituent of an $R^1$ group is a quaternary ammonium group, this may typically be a group of the formula $—N+(R^2)_3(X^3)^-$, wherein each $R^2$ is alkyl or aryl, typically alkyl; and $X^3$ is any convenient anion. However, such $R^1$ substitution is not so limited and the skilled person will be aware of the possibility of substituting $R^1$ with more structurally complicated quaternary ammonium moieties such as alkylene- or alkyleneoxy-linked imidazolium and pyrrolidinium cations.

Where a substituent of an $R^1$ group is a PEG-containing substituent, wherein PEG comprises a plurality, e.g. 2 to 2000, consecutive units of $—CH_2CH_2O—$, typically only one of $P^1$ and $P^2$ will be substituted in this way.

Catalysts comprising sulfonate ($—SO_3^-$), phosphate ($—OPO_3^{2-}$), carboxylate ($—CO_2^-$) or quaternary ammonium groups or PEG-containing substituents can be advantageous, as is known in the art, in permitting metatheses to be effected in water and/or protic solvents such as alcohols (for example $C_{1-6}$ alcohols such as methanol or ethanol), or combinations of such solvents or mixtures of other solvents with other solvents with which these solvents or mixtures of solvents are miscible, for example dimethylformamide (DMF) and dimethyl sulfoxide (DMSO). Catalysts comprising sulfonate ($—SO_3^-$), phosphate ($—OPO_3^{2-}$), carboxylate ($—CO_2^-$) or quaternary ammonium groups also may be used to effect metathesis catalysis in ionic liquids, as described in more detail below. Introduction of each of these substituents into $R^1$ groups is within the capability of those skilled in the art and, in this regard, reference is made to the technology described in section 9 of the article by GC Vougioukalakis and RH Grubbs (supra), and the references cited therein. The skilled person will understand that the teaching in this reference (in relation to substitution of NHC-containing catalysts, both on the NHC ligands themselves as well as other parts of alkylidene ruthenium metathesis catalysts, may be applied mutatis mutandis to phosphorus-containing ligands in accordance with the present invention. For example, there is described in WO 01/46096 (Sasol Technology (Pty) Ltd) an alkylidene ruthenium metathesis catalyst comprising two dicyclohexyl ((trimethylammonium) ethyl)phosphine ligands having solubility in both water and methanol.

Where the substituent of a $R^1$ group is a quaternary ammonium group, the nature of the counteranion (to the quaternary ammonium group) is not of particular consequence. Any convenient anion may be used. Halide anions such as chloride anions are typical although the skilled person will be able to identify other suitable anions without difficulty.

Whilst substitution with a sulfonate, phosphate or carboxylate group is advantageous in the context of conducting metathesis reactions in solutions comprising water and/or protic solvents, as discussed supra, in which the identity of the countercation to these groups is not of particular importance, and may for example be an alkali or alkaline earth cation (such as $Na^+$, $Li^+$, $K^+$ or $Ca^{2+}$, for example), the introduction of such substituents also offers the possibility of conducting metathesis reactions in ionic liquids, in particular with the group is sulfonate.

The alkylidene group (=A in formula (I)) may be any suitable alkylidene group for use in ruthenium-catalysed metathesis. The skilled person is aware of a wealth of information regarding the various possibilities for the alkylidene group, as well as methods of making such alkylidene-containing catalysts. In this regard, reference is made yet again to G C Vougioukalakis and R H Grubbs (supra), as well as P Schwab et al. (*J. Am. Chem. Soc.* 1996, 118, 100-110) and P Schwab et al. (*Angew. Chem., Int. Ed. Engl.*, 1995, 34, 2039-2041) and the description throughout these publications of various possibilities for the alkylidene group in catalysts of this type, including the variants expressly described in section 5 of Vougioukalakis and Grubbs. Typically, the alkylidene group may be defined as a moiety of formula $=CR^yR^z$, wherein "=C" indicates the bonding with the ruthenium ion. One of $R^y$ and $R^z$ may be hydrogen and either or both of $R^y$ and $R^z$ may be alkyl, alkenyl, alkynyl, aryl carboxyalkyl, alkoxy, alkenyloxy, alkynyloxy or alkoxycarbonyl, or $R^y$ and $R^z$ together form a saturated, unsaturated or aromatic cyclic or bicyclic moiety. Those of skill in the art will recognise that, where $R^y$ and $R^z$ together form a bicyclic moiety, this embraces the indenylidene alkylidenes first reported by Nolan et al. in 1999, and which are often employed in contemporary metathesis catalysis, in particular the 3-phenyl-1H-inden-1-ylidenes. According to particular embodiments, the alkylidene group may be indenylidene, for example an aryl-, e.g. phenyl-, substituted indenylidene, e.g. 3-phenyl-1H-inden-1-ylidene. However, the invention should in no way be considered to be so-limited. For example, the alkylidene group may embrace moieties of formula =$CR^yR^z$, wherein $R^y$ is hydrogen, alkyl or aryl and $R^z$ is alkyl, alkenyl or aryl, more particularly wherein $R^z$ is phenyl or vinyl, either an unsubstituted or substituted with halo, nitro, amino (e.g. dimethylamino), alkyl (e.g. methyl), alkoxy (e.g. methoxy) and aryl (e.g. phenyl). As an example, the alkylidene group may be benzylidene (the moiety of formula =CH(Ph)), which is the alkylidene moiety in Grubbs' First Generation catalyst (1, supra) and others.

The alkylidene ruthenium catalysts used may be formed in situ or ex situ. Catalysts prepared ex situ are often referred to in the art as being well-defined. "Well-defined" means, as is understood by those skilled in the art, and is meant herein, a complex that is prepared ex situ, and is thus susceptible to characterisation (i.e. definition). In other words, the use of a well-defined complex means that the environment, for example, a reaction vessel, in which the substrate(s) for the ethenolysis reaction are contacted with the catalyst of formula (I) is charged a pre-formed transition metal catalyst of formula (I), rather than precursors to such transition metal complexes formed in situ.

Alternatively, as is known, the catalyst of formula (I) may be formed in situ. Reference is made in this regard, for example, to P O Nubel and C L Hunt (*J. Molec. Catal. A: Chemical*, 1999, 145(1-2), 323-327) and U.S. Pat. No. 6,159,890, which describe catalyst systems from which catalytically active species may be generated in situ. As is described in these publications, a source for the ruthenium ion in the metathesis catalyst, as well as sources of the desired neutral ligands (which according to the present invention may be the phosphorus-coordinating ligands $P^1$ and $P^2$ described herein), anionic ligands and for the alkylidene group, are brought into contact. In such in situ embodiments, the method of the invention will thus typically involve bringing together these components in an environment, for example, a reaction vessel, in which the substrates for the metathesis reaction are to be contacted.

The source of the ruthenium ion is typically an inorganic salt such as ruthenium halide, e.g. chloride, for example ruthenium (III) chloride, optionally as a hydrate thereof. Advantageously, such salts also provide anionic ligands $X^1$ and $X^2$, i.e. where these ligands are the halide ions of the ruthenium halide. Alternatively, they may be introduced separately.

The source of the alkylidene A may be an alcohol. For example, where the alkylidene is 3-phenyl-1H-inden-1-ylidene, this may be made by a reaction between a source for the ruthenium (II) ion within the catalyst of formula (I) and 1,1-diphenyl-2-propyn-1-ol. The skilled person is well aware of how to make ruthenium indenylidene complexes (see, for example, F Boeda et al. (Chem. Commun., 2008, 2726-2740).

The source of the ruthenium ion is typically an inorganic salt such as ruthenium halide, e.g. chloride, for example ruthenium (III) chloride, optionally as a hydrate thereof. Advantageously, such salts also provide anionic ligands $X^1$ and $X^2$, i.e. where these ligands are the halide ions of the ruthenium halide. Alternatively, they may be introduced separately.

Whilst it is possible to make catalysts of formula (I) in situ, this is not at all essential, the synthesis of well-defined alkylidene ruthenium catalysts for use in the present invention, including those of formula (I), being at the disposal of the skilled person. Moreover, such catalysts are readily available commercially, for example from Umicore AG & Co. KG, Germany, and other suppliers of metathesis catalysts with which the skilled person is very familiar. Specific examples of catalysts include the First Generation catalysts dichloro(3-phenyl-1H-inden-1-ylidene)bis(tricyclohexylphosphine) ruthenium (II) and (3-phenyl-1H-iden-1-ylidene)bis(isobutylphobane) ruthenium (II), sold as M1 and $M1_1$ respectively by Umicore.

Mention is now made of the nature of the monoalkene substrate for the ethenolysis reaction, and of the ethenolysis reaction itself By ethenolysis reaction is meant, as the term is understood by those in the art, a metathesis reaction between ethylene and an internal alkene. By internal alkene is meant that neither carbon atom of the carbon-carbon double bond of the alkene has two hydrogen atoms attached to it. The internal alkenes that are subjected to ethenolysis in accordance with the present invention are monoalkenes, by which it is meant that there is only one alkenic carbon-carbon double bond in such compounds.

According to particular embodiments, the monoalkene substrate for the ethenolysis reaction is located within a hydrocarbylene chain, optionally interrupted with ether, ester, amide or amine groups, comprising from about 4 to about 100, e.g. from about 8 to about 30 carbon atoms. The optionally interrupted hydrocarbylene chain may be optionally substituted. In many embodiments, however it is unsubstituted. In many of these embodiments, it is also not interrupted, i.e. is a hydrocarbylene chain that consists only of carbon and hydrogen atoms.

According to particular embodiments, each carbon atom of the carbon-carbon double bond of the monoalkene is attached to a typically unbranched, optionally interrupted hydrocarbyl group, the carbon atoms of which are optionally interrupted with ether, ester, amide or amine groups, each of which groups comprise between 1 and about 25, more typically between about 1 and 10 atoms, from the first atom of the hydrocarbyl group attached to the carbon-carbon bond and its terminal carbon atom. These optionally interrupted hydrocarbyl groups may be optionally substituted. In some embodiments, however, they are unsubstituted. In other embodiments, one is substituted and one is not. In many of these embodiments, neither is interrupted, with one hydrocarbyl group being an uninterrupted, unsubstituted hydrocarbyl group and the other an uninterrupted, substituted hydrocarbyl group.

According to particular embodiments of the invention, the carbon-carbon double bond of the monoalkene is a disubstituted carbon-carbon double bond (i.e. is of formula —CH=CH—). According to these and other embodiments of the invention, each carbon atom of the carbon-carbon double bond is attached to an alkylene or alkyl moiety each of which independently comprises from 2 to 7 carbon atoms.

For example, the carbon-carbon double bond may be flanked on either side by two ethylene (—CH$_2$CH$_2$—) moieties, by two propylene (—CH$_2$CH$_2$CH$_2$—) moieties or by one propylene moiety and one ethylene moiety.

According to particular embodiments of the invention, the monoalkene is an optionally esterified monounsaturated fatty acid, for example a fatty acid comprising from 4 to 28 carbon atoms. As is known, a fatty acid is a member of the series of open-chain carboxylic acids including those found as esters in fats and oils. A monounsaturated fatty acid may be regarded as a carboxylic acid comprising an alkenyl group having one carbon-carbon double bond. Most naturally occurring fatty acids—it being understood that fatty acids need not be naturally occurring—comprise an even number of carbon atoms.

According to particular embodiments of the invention, the monounsaturated fatty acid comprises from 14 to 18 carbon atoms. The carbon-carbon double bond of these and other monounsaturated fatty acids may be a cis or trans C=C bond. According to particular embodiments, the carbon-carbon double bond of the fatty acid is a trans C=C bond. Examples of monoalkene substrates for the ethenolysis may be selected from the group consisting of oleic acid, sapienic acid, palmitoleic acid, myristoleic acid or erucic acid, and esters thereof. According to particular embodiments of the invention, the monoalkene substrate is oleic acid or an ester thereof.

Where reference is made to esters of carboxylic acids herein, in particular esters of monounsaturated fatty acids, these esters may be alkyl or aryl esters. The alkoxy or aryloxy moieties in these alkyl or aryl esters may be substituted or unsubstituted. According to particular embodiments, these alkyl or aryl groups are unsubstituted. According to more particular embodiments, the ester may be a phenyl ester or an alkyl ester. According to still more particular embodiments, the alkyl ester is a C$_{1-6}$ alkyl ester, for example, methyl, ethyl or n- or isopropyl.

According to a specific embodiment, the monoalkene is methyl oleate, the ethenolysis of which affords two industrially important chemicals: 1-decene and methyl 9-decenoate. Other commercially relevant feedstocks may be provided by ethenolysis of other monounsaturated fatty acids, including those described herein, and other internal monoalkenes.

According to further embodiments, the carbon-carbon double bond of the monoalkene is tethered to an aromatic moiety. By "tethered" is meant that the carbon-carbon double bond is connected to a ring atom of the aromatic moiety, analogously to the carbon-carbon double bond in a monounsaturated fatty acid being tethered to the carboxylic acid thereof. The aromatic moiety may be monocyclic or polycyclic. According to particular embodiments, the aromatic moiety is an optionally substituted monocyclic aromatic moiety, for example an optionally substituted phenyl group.

According to particular embodiments, the aromatic moiety may be an aromatic alcohol. According to such embodiments, the carbon-carbon double bond may be tethered to either the same ring to which the hydroxyl group of the aromatic alcohol is attached, or to a ring fused thereto. The carbon-carbon double bond may in some embodiments be directly attached to the ring atom of the aromatic alcohol. Typically, however, it is connected to ring atom of the aromatic alcohol by a typically straight-chain hydrocarbylene, optionally interrupted with ether, ester, amide or amine groups, wherein between 1 and about 25, more typically between about 1 and 10 atoms, separate the carbon-carbon double bond from the aromatic ring. The optionally interrupted hydrocarbylene chain may be optionally substituted. In many embodiments, however, it is unsubstituted. In many of these embodiments, it is also not interrupted, i.e. is a hydrocarbylene chain. In particular embodiments, such an uninterrupted, unsubstituted hydrocarbylene chain is an alkylene chain comprising between 1 and about 25, more typically between about 1 and 10, carbon atoms between the carbon-carbon double bond and the ring atom of the aromatic alcohol to which the hydrocarbylene chain is attached.

In those embodiments of the invention in which the carbon-carbon double bond of the monoalkene is tethered to a carboxylic acid or an aromatic moiety, the carbon atom of the carbon-carbon double bond that is not so tethered is connected to a typically unbranched hydrocarbyl group, the carbon atoms of which are optionally interrupted with ether, ester, amide or amine groups, comprising between 1 and about 25, more typically between about 1 and 10 atoms, from the first atom of the hydrocarbyl group attached to the carbon-carbon bond and its terminal carbon atom. This optionally interrupted hydrocarbyl group may be optionally substituted. In many embodiments, however, it is unsubstituted. In many of these embodiments, it is also not interrupted, i.e. is a hydrocarbyl group consisting of carbon and hydrogen atoms. In particular embodiments, such an uninterrupted, unsubstituted hydrocarbyl group comprises between 1 and about 25, more typically between about 1 and 10, carbon atoms.

According to further embodiments of the present invention, the monoalkene may be a cycloalkene for example a C$_{6-10}$cycloalkene, for example cyclohexene or cyclooctene.

By "aromatic alcohol" is meant herein a compound of formula R$^3$OH in which R$^3$, to which the hydroxy group is attached, is an aromatic ring. As stated above, the term aromatic embraces within its scope heteroaromatic. The complement to heteroaromatic, whereby to refer to aromatic compounds not comprising any heteroatoms in the aromatic ring, is to refer to aromatic hydrocarbons. It should be noted that use of this term does not exclude the possibility that such aromatic compounds are substituted with heteroatom-containing substituents. Typically, R$^3$ is an optionally substituted aromatic hydrocarbon, by which is meant that the aromatic hydrocarbon may comprise one or more additional substituents over and above the alkene-containing moiety and the hydroxyl group.

The aromatic ring to which the hydroxyl group of the aromatic alcohol is attached may be a monocycle, i.e. in which the aromatic ring to which the hydroxyl group is fused is not fused to any other rings. Alternatively, this aromatic ring may be part of a polycyclic system, i.e. in which it is fused to one or more aromatic (including heteroaromatic) or non-aromatic rings. Napthalene, anthracene and phenanthrene are examples of fully aromatic polycyclic hydrocarbons (a bicycle and two tricycles respectively), and benzimidazole is an example of a fully aromatic polycyclic heteroaromatic compound. 1,2,3,4-tetrahydronaphthalene is an example of a compound comprising an aromatic ring fused to a non-aromatic ring.

Typically, when the hydroxyl-bearing aromatic ring is part of a polycyclic system, this will be a fully aromatic system. Examples of such aromatic alcohols include, for example, napthol (1- or 2-) and phenanthrol (e.g. 9-phenanthrol).

Whilst the hydroxy-substituted aromatic ring of the aromatic alcohol may be part of a polycyclic system, in many embodiments the aromatic alcohol is monocyclic, that is to say the hydroxy-substituted aromatic ring is not fused to another ring. Within these embodiments of the invention, the hydroxy-substituted aromatic ring may be a phenol.

The aromatic alcohol may be subject to additional substitution (i.e. over and above the C=C-containing substituent). Such substituents may be, for example, those mentioned above with which aromatic moieties may be substituted, for example halo, alkyl, aryl, hydroxy, nitro, amino, alkoxy, cyano, formyl, ester, acyl, amido, carbamido and sulfonamide. For example, the aromatic alcohol may be an aromatic diol or a hydroxybenzoic acid.

According to a particular embodiment of the invention, the ethenolysis may be of a specific component of cardanol, a material found in cashew nut shell liquid (CNSL), the byproduct of the cashew nut processing industry, which is available in an amount of approximately 300,000-600,000 tonnes per year worldwide and which has so few uses that it is generally considered to be a waste stream.

CNSL predominantly comprises four phenolic compounds, three of which predominate, the proportions of which vary naturally and also depend on the method by which CNSL is extracted from the shells of the cashew nuts. Typical compositions of CNSL (with the figures being molar percentages) obtained by solvent extraction or by roasting are indicated in Table A below:

it will be understood from the numbering (1)-(4) and lettering (a)-(d) employed in Table A that compound 2b, for example, denotes the monoalkene component of cardanol and compound 2 denotes cardanol, i.e., the mixture of compounds.

Solvent extraction of the nuts gives predominately anacardic acid whilst roasting of the nuts gives mainly cardanol (2), owing to the decarboxylation of anacardic acid on heating. As may be appreciated from Table A, all four components have a fifteen carbon linear chain in the meta-position to the phenolic group with a varying degree of saturation, dependant on the origin of the cashew nuts.[2-4]

Anacardic acid (1) can be isolated from CNSL by precipitation with calcium hydroxide. Separation and acidification of the calcium anacardate gives the pure acid 1, which can be transformed to cardanol (2) by heating to 200° C.[5] Further purification by vacuum distillation gives pure cardanol (2) without alteration of the side-chain. Its versatility as a renewable starting material arises from its structure. Owing to the phenol group and the unsaturated side-chain in the meta-position, it can be easily modified to valuable chemicals by introducing novel functionalities, hence the particular discussion herein of the carbon-carbon double bond of the monoalkene subject to ethenolysis according to the present invention being tethered to an aromatic moiety in particular an aromatic alcohol.

Several applications of cardanol (2) or CNSL are known. For example, the synthesis of biscardanol derivatives as monomers, additives in surface coatings and resins' and the synthesis of sodium cardanol sulfate as detergents.[7] 2 can also be functionalised to its corresponding ethers, which have been used as polymer additives[8] or in nanofibers.[9] However, the selective homogeneous catalysed transformation of cardanol (2) to valuable intermediates is only rarely described and just few examples like the double bond metathesis of cardanol (2) exist.[6, 9] Owing to its unsaturated

TABLE A

Typical composition of CNSL obtained by solvent extraction or by roasting.

| Component:- | Anacardic acid (1) | Cardanol (2) | Cardol (3) | 2-Methylcardol (4) |
|---|---|---|---|---|
| Solvent extraction | 65 | 10 | 15 | Trace |
| Roasting | 10 | 85 | 3 | 2 |

(Legend to Table A overleaf)
R is a $C_{15}$ hydrocarbyl chain with 1 to 3 double bonds, "*" indicating the end of the bond through which the hydrocarbyl chains —R below are attached to the aromatic ring:

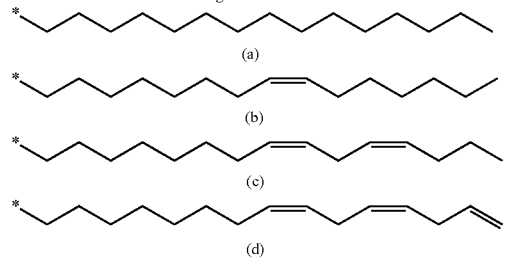

side-chain, metathesis is an attractive tool for functionalising 2 to intermediates of higher added-value. Vasapollo et al. reviewed the transformation of cardanol 2 to new fine chemicals as well as new hybrid functional materials, such as cardanol porphyrins, cardanol phthalocyanines and cardanol fullerenes via olefin-metathesis.[9] However, no applications of the newly synthesised materials have been reported.

It is thus of particular interest to convert cardanol (2) selectively to intermediates, which can be used directly as substitutes in the value-added chain. For example, the products of ethenolysis of cardanol monoene (2b) are 3-non-8-enylphenol (4) and 1-octene (6), each of which is a potentially important product. 1-Octene 6, is mainly used as a comonomer for polyethylene and 3-nonylphenol has the potential for replacement of the 4-nonylphenol, which makes an excellent detergent via ethoxylation, but has been banned in Europe because of its endocrine disrupting properties.[12, 13]

In the experimental section below, there is described a detailed study of the selective ethenolysis of cardanol (2). Unexpectedly, first generation catalysts in particular give very high selectivities to the desired products and very high conversions. We also report oestrogenicity studies on 3-nonyl phenol, which show that it is 2 orders of magnitude less oestrogenic than 4-nonylphenol.

As is discussed by J A Mmongoyo et al. (supra), cardanol is generally used in the art, and is used in the same sense herein, to refer to a composition comprising a mixtures of compounds in which hydrocarbyl chain R varies in its degree of unsaturation, as indicated in Table A above. Similarly, the other components of CNSL, anacardic acid, cardol and 2-methylcardol are also used to refer to mixtures of compounds in which hydrocarbyl chain R of Table A varies in its degree of unsaturation The versatility of the components of CNSL, including but not limited to cardanol, as starting materials in synthesis arises from their structure and, amongst other reactions J A Mmongoyo et al. discuss, cross metathesis between ethylene and the unsaturated components within cardanol may be used to afford 1-octene and 3-non-8-enylphenol.

According to particular embodiments of the invention the method comprises contacting the monoalkene component of cardanol:

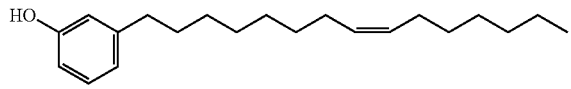

(2b)

with an alkylidene ruthenium alkene or other metathesis catalyst described herein. According to particular embodiments, the method comprises contacting this monoalkene with an alkylidene ruthenium alkene metathesis catalyst. In this way, the invention permits the preparation of 1-octene and 3-non-8-enylphenol. It will be understood from the foregoing discussion that the latter of these may be used as a potential detergent precursor.

The monoene component of cardanol, which may, for example, be prepared by selective transfer hydrogenation using $RuCl_3 \cdot xH_2O$, as described by Perdriau et al. (S. Perdriau, S. Harder, H. J. Heeres and J. G. de Vries, *Chem Sus Chem*, 5, 2427 (2012)), who report the selective transfer hydrogenation of cardanol to its monounsaturated component. The transfer hydrogenation gives access to almost pure cardanol monoene, although some double bond isomerisation occurs during the transfer hydrogenation reaction.

According to particular embodiments, where a 3-non-8-enylphenol, for example 3-non-8-enylphenol, is prepared, this may be optionally subject to hydrogenation of the carbon-carbon double bond, whereby to provide a 3-nonylphenol, and further, ethoxylation of the phenol to provide an ethoxy-3-nonylphenol or oligoethoxy-3-nonylphenol, in which the phenol hydroxyl is replaced with $-(OCH_2CH_2)_n$OH, wherein n is an integer of between 1 and 20, typically between 3 and 15, e.g. 9. Suitable methods of hydrogenation and ethoxylation are well within the capability of those skilled in the art. The invention also extends to ethoxy-3-nonylphenol or oligoethoxy-3-nonylphenol obtainable or obtained by the method of the invention. Prior to hydrogenation, the 3-non-8-enylphenol may be subject to optional purification from other components (e.g. cyclohexadiene or other diene and/or 1-octene) resultant from the ethenolysis reaction by which it is prepared, according to the normal ability of those skilled in the art. Similarly, 1-octene may be readily subject to optional purification from other components (e.g. cyclohexadiene or other diene and/or 3-non-8-enylphenol) resultant from the ethenolysis reaction by which it is prepared.

A characterising feature of the present invention is the presence of the diene during the ethenolysis of the monoalkene. In particular, according to the method of the first aspect of the invention, the diene is introduced into the reaction vessel in which the ethenolysis reaction is conducted. Generally, at least the monoalkene and ethylene are also introduced into the reaction vessel in which the ethenolysis reaction is conducted. By being "introduced into" is explicitly meant that the material concerned is transferred from outside the reaction vessel to inside the reaction vessel in which the ethenolysis reaction takes place. In other words, the diene, or other material that is introduced into the reaction vessel, is not generated in situ. From the foregoing discussion, it will be understood that, according to some embodiments, the ethenolysis catalyst is introduced into the reaction vessel. According to other embodiments it is generated in situ.

The diene used need not be particularly limited, provided of course it comprises two nonaromatic carbon-carbon double bonds. Typically, however, it will be a hydrocarbyl diene, i.e. a diene consisting only of carbon and hydrogen atoms, typically comprising from 4 to 10 carbon atoms, for example from 6 to 8 carbon atoms. According to these and other embodiments of the invention, the diene may be cyclic. According to more specific embodiments, the diene may be selected from the group consisting of 1,4-cyclohexadiene, 1,4-hexadiene, 1,5-cyclooctadiene and 1,7-cyclooctadiene. According to specific embodiments the diene is 1,4-cyclohexadiene.

The skilled person will be able to ascertain without undue burden appropriate quantities of diene to introduce for any given ethenolysis reaction. For example, typical amounts are in the range of 0.01 to 1 molar equivalents with respect to the monoalkene, for example between about 0.05 and about 0.5 molar equivalents.

It will be understood that the introduction of a diene into a reaction vessel in which cardanol (i.e. mixture 2) is subject to ethenolysis constitutes an embodiment of the invention.

General conditions for effecting ethenolysis reactions are well-known and an illustrative procedure is described in the examples below. Typically, the reactions will be conducted at temperatures ranging from about 10° C. to about 100° C. for example from about 20° C. to about 70° C., dependent on solvent and other factors, for between about 5 minutes and 24 hours, typically between about 1 hour and about 8 hours. (It will, however, be appreciated that ethenolysis may be conducted at higher temperatures, for example when using ionic liquids as solvents (vide infra). When conducting ethenolysis reactions, pressurised reactors such as autoclaves for Fisher-Porter tubes or bottles are typically used, the pressure at which the reaction is conducted generally being in the range of about 1 bar (100 kPa) to about 100 bar (10,000 kPa), for example in the range of about 5 bar (500 kPa) to about 15 bar (1,500 kPa).

As noted above, substitution of the $P^1$ and/or $P^2$ groups (of the relevant alkylidene ruthenium catalysts described herein) with a charged or PEG-containing moiety offers the opportunity to conduct the desired ethenolysis reactions in water and/or protic solvents. Whilst substitution with a sulfonate, phosphate, carboxylate or quaternary ammonium group is advantageous in the context of conducting ethenolysis reactions in solutions comprising such solvents, in which the identity of the countercation to the negatively charged groups is not of particular importance, and may for example be an alkali or alkaline earth cation (such as $Na^+$, $Li^+$, $K^+$ or $Ca^{2+}$, for example) and the identity of the counteranion to the quaternary ammonium group is also not of particular importance, and may for example be halide anion (such as $Cl^-$, for example), the introduction of such substituents also offers the possibility of conducting ethenolysis reactions in ionic liquids.

Ionic liquids have in recent years been found to be of utility in a wide variety of synthetic applications. These liquids can be advantageous for use as solvents or as other types of continuous liquid phase reaction media (as discussed further below) on account of their thermal stability, inflammability and lack of volatility. The nature of ionic liquids is well known to those of skill in the art. Broadly speaking, an ionic liquid is salt, but one in which the ions are insufficiently well-coordinated for the compound to be other than a liquid below 150° C., more usually below 100° C., and in some embodiments even at room temperature—so-called room-temperature ionic liquids. In other words, ionic liquids are salts that form stable liquids at temperatures below 150° C. or lower. There are no particular limitations as to the specific types of ionic liquids that may be used as solvents for ethenolyses in accordance with the present invention. One or more ionic liquids may be used. As will be readily understood, one of the specific advantages that use of ionic liquids confers is removal of the need to have a condenser in order to achieve a high-temperature liquid environment in which the method of the present invention may be conducted. Ionic liquids, with inherently low vapour pressure, allow the maintenance of constant temperature to be achieved over the course of the method of the invention, in contrast to the significant vapour pressures of the high-boiling point solvents typically used in the prior art. Such solvents inevitably cause a decrease in the temperature of a reaction vessel when the solvent condenses back in. Ionic liquids, therefore, permit not only an advantageously elevated temperature but allow a more homogeneous temperature to be maintained throughout the reaction. Typically, ionic liquids have either no, or negligible, vapour pressure.

Organic cations that may be present in ionic liquids may include, for example, quaternary ammonium, phosphonium, heteroaromatic, imidazolium and pyrrolidinium cations. The counteranions present in ionic liquids are likewise not particularly limited. For example, suitable anions include halide (e.g. chloride or bromide), nitrate, sulfate, hexafluorophosphate, tetrafluoroborate, bis(triflylmethylsulfonyl)imide, (the bis(triflylmethylsulfonyl)imide anion being abbreviated here as $[NTf_2]$; it is also sometimes referred to as $N[Tf]2$ or $[Tf]2N$) anions. Others will be evident to those of skill in the art.

Ionic liquids that may be used include 1-alkyl-3-methylimidazolium bis(trifluoromethylsulfonyl)imide, 1-alkyl-3-methylimidazolium hexafluorophosphate, 1,1,3,3-tetralkylguanidinium lactate, alkylpyridinium tetrafluoroborate, 1-alkyl-3-alkylimidazolium tetrafluoroborate, 1-alkyl-3-alkylimidazolium bis(trifluoromethyl sulfonyl)imide 1-alkyl-3-alkylimidazolium tetrafluoroborate, trialkyl-n-tetradecylphosphonium bis(trifluoromethylsulfonyl)imide, 1-alkyl-1-alkyl-pyrrolidinium trifluoromethanesulfonate and thiol-functionalised ionic liquids, wherein each alkyl is independently $C_{1-20}$, for example $C_{2-20}$ or $C_{2-12}$. For example the ionic liquids may be 1-butyl-3-methylimidazolium bis(trifluoromethylsulfonyl)imide, 1-n-butyl-3-methylimidazolium hexafluorophosphate, 1,1,3,3-tetramethylguanidinium lactate, N-butylpyridinium tetrafluoroborate, 1-butyl-3-methylimidazolium tetrafluoroborate, 1-ethyl-3-methylimidazolium bis(trifluoromethyl sulfonyl)imide 1-ethyl-3-methyl-imidazolium tetrafluoroborate, tri-n-hexyl-n-tetradecylphosphonium bis(trifluoromethylsulfonyl)imide, 1-butyl-1-methyl-pyrrolidinium trifluoromethanesulfonate, all of the foregoing but in which the cation is instead 1-octyl-3-methylimidazolium; and thiol-functionalised ionic liquids. Ionic liquids are readily available commercially, e.g. from Cytec Industries, Inc. and by contractual arrangement with the Ionic Liquids Laboratory at the Queens University of Belfast (see quill.qub.ac.uk for further details).

Ionic liquids can be engineered to tune their advantageous properties such as stability, vapour low pressure and solvating ability so as to be safer and more environmentally friendly than conventional volatile, organic compounds. Consequentially, and because of the possibility of recycling, use of ionic liquids can simplify synthetic reactions when it is possible to substitute such ionic liquids for conventional solvents.

As is known by those skilled in the art, certain ionic liquids are, notwithstanding their advantages, susceptible to decomposition at elevated temperatures (for example in excess of 240° C.) in a normal oxygen-containing atmosphere. However, such decomposition may be mitigated where heating is conducted in an inert atmosphere. Suitable inert atmospheres (e.g. those from which oxygen and/or moisture is substantially excluded) may be achieved by means well known to those of skill in the art and may be provided through the use of purging using argon, nitrogen or other gases. In certain embodiments, heating of mixtures to temperatures of approximately 100 to 150° C. may be effected in order to remove any residual oxygen or moisture prior to subsequent use.

Where the method of the invention is not conducted in an ionic liquid, the reaction may be carried out in any convenient solvent. Protic solvents such as alcohols may be used, as may aprotic solvents including chlorinated solvents such as dichloromethane; hydrocarbon solvents such as hexane mixtures or toluene as appropriate; or others (e.g. ethers such as diethyl ether and tetrahydrofuran (THF); ketones such as acetone or butanone; and esters such as ethyl acetate). According to particular embodiments of the invention, the solvent used may be a chlorinated solvent such as dichloromethane. However, use of such solvents is not by any means mandatory and the ethenolysis reactions may equally be practised with use of non-chlorinated solvents, for example toluene.

The selection of an appropriate solvent is well within the capability of a person of normal skill. Alternatively, as is known to those familiar with metathesis chemistry, it may be appropriate to conduct ethenolysis reactions of the invention in the absence of solvent. As with many other aspects of the method of the invention, the skilled person is well able to establish appropriate reaction conditions within his normal skill.

The method of the invention may be conducted in batch processing, i.e. in which the desired reactant(s) for the metathesis reaction is/are introduced into a suitable vessel, for example an autoclave, in view of the use of ethylene in accordance with the invention.

Alternatively, the method of the invention may be conducted on a non-batch, e.g. continuous flow basis. Such non-batch methods may be achieved by dissolving well-defined catalysts in ionic liquids, e.g. in a reactor, and introducing the substrate(s) for the metathesis reaction in supercritical carbon dioxide.

Continuous processing is described by P B Webb et al. (*J. Am. Chem Soc.,* 2003, 125, 15,577-15,588) in connection with hydroformylation of alkenes in supercritical fluid-ionic liquid biphasic systems. However, the skilled person will understand that the principles described therein as to how appropriate solubility of catalyst in ionic liquid may be achieved are applicable to the present invention. In particular, the use of appropriate salts of sulfonated phosphines is discussed in order to achieve effective solubility of catalysts in ionic liquid. The skilled person will likewise understand that the teachings by Webb et al. may be applied to sulfonated phosphites, phosphonates or phosphinates as well as phosphines, and to phosphines, phosphites, phosphonates and phosphinates bearing phosphate or carboxylate moieties, so as to maximise solubility in the ionic liquid and thereby activity of the resultant catalysts.

Another example of continuous processing, again of hydroformylation, is described by U Hintermair et al. (*Dalton Trans.,* 2010, 39, 8501-8510). In this publication, microporous silica-supported catalysts prepared from mono-sulfonated triphenylphosphine with an imidazolium cation and an ionic liquid are described as being used in the continuous flow hydroformylation of 1-octene in the presence of compressed carbon dioxide. In this way, continuous flow of near critical or supercritical carbon dioxide allowed continuous flow hydroformylation to be effected and it will be understood that the same principles described in this publication may also be applied to the metathesis reactions to which the present invention is directed. Reference is further made to the description of continuous flow homogeneous alkene metathesis in a similar system (see R Duque et al., *Green Chem.,* 2011, 13, 1187-1195).

It will be readily appreciated by those skilled in the art that, if desired, recognised methods of immobilisation of the catalysts described herein can be used to generate heterogeneous catalysts which retain the important features of the metathesis catalysts described herein, for example the phosphorus-coordinating ligands or catalysts may be absorbed onto a suitable solid support or reacted with such a support to form a covalently bound ligand or catalyst.

All publications (both patent and non-patent) referred to herein are hereby incorporated by reference in their entirety.

The invention may be further understood with reference to the following non-limiting clauses:

1. A method of ethenolysis of a monoalkene, comprising introducing into a reaction vessel a monoalkene and a diene, and subjecting the monoalkene to ethenolysis in the presence of a metathesis catalyst and the diene.
2. The method of clause 1, wherein the metathesis catalyst is an alkylidene ruthenium alkene metathesis catalyst.
3. The method of clause 1 or clause 2 wherein the carbon-carbon double bond of the monoalkene is a disubstituted carbon-carbon double bond.
4. The method of any one preceding clause, wherein each carbon atom of the carbon-carbon double bond is attached to an alkylene or alkyl moiety each of which independently comprises from 2 to 7 carbon atoms.
5. The method of clause 4 wherein the carbon-carbon double bond is flanked by two ethylene moieties.
6. The method of clause 4 wherein the carbon-carbon double bond is flanked by two propylene moieties.
7. The method of any one preceding clause, wherein the monoalkene is an optionally esterified monounsaturated fatty acid.
8. The method of clause 7, wherein the fatty acid comprises from 4 to 28 carbon atoms.
9. The method of clause 8, wherein the fatty acid comprises from 14 to 18 carbon atoms
10. The method of any one of clauses 7 to 9 wherein the carbon-carbon double bond is a cis C=C bond.
11. The method of any one of clauses 7 to 9 wherein the carbon-carbon double bond is a trans C=C bond.
12. The method of clause 7 wherein the fatty acid is selected from the group consisting of oleic acid, sapienic acid, palmitoleic acid, myristoleic acid or erucic acid.
13. The method of clause 12, wherein the fatty acid is oleic acid.

14. The method of any one of clauses 7 to 13, wherein the fatty acid is esterified 15. The method of clause 14, wherein the esterified fatty acid is an alkyl, aryl or heteroaryl ester.

16. The method of clause 15, wherein the esterified fatty acid is an alkyl ester.

17. The method of clause 7, wherein the monoene is methyl oleate.

18. The method of any one of clauses 1 to 6, wherein the carbon-carbon double bond of the monoalkene is tethered to an aromatic moiety.

19. The method of clause 18, wherein the aromatic moiety is an aromatic alcohol

20. The method of clause 19 wherein the aromatic alcohol is a phenol or a napthol.

21. The method of clause 19 wherein the aromatic alcohol is a phenol.

22. The method of any one of clauses 18 to 21, wherein the carbon-carbon double bond is tethered to the aromatic alcohol by a optionally substituted hydrocarbylene chain, which is optionally interrupted with ether, ester, amide or amine groups.

23. The method of any of clauses 18 to 22 wherein the method comprises the ethenolysis of cashew nut shell liquid, or one or more components thereof.

24. The method of any one of clauses 18 to 23, wherein the method comprises the ethenolysis of cardanol.

25. The method of clause 23 wherein the method comprises the ethenolysis of a monoene component of cardanol.

26. The method of clause 23, wherein the method comprises the ethenolysis of

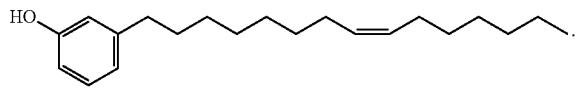 [SMILES: CCCCCC/C=C\CCCCCCCc1cccc(O)c1]

27. The method of any one of clauses 23 to 26, which is a method for preparing 1-octene.

28. The method of any one of clauses 18 to 26, which is a method of preparing 3-non-8-enylphenol.

29. The method of clause 28 further comprising hydrogenating 3-non-8-enylphenol and ethoxylating the resultant 3-nonylphenol to provide ethoxy-3-nonylphenol or oligoethoxy-3-nonylphenol, in which the -oligoethoxy substituent is of formula —$(OCH_2CH_2)_nOH$, wherein n is an integer of between 1 and 20.

30. The method of any one preceding clause wherein the alkylidene ruthenium alkene metathesis catalyst comprises two ligands $P^1$ and $P^2$, which may be the same or different and of formula $P(R^1)_3$, in which P is a phosphorus atom coordinated to the ruthenium ion and each $R^1$ is independently an optionally substituted alkyl or alkoxy group; or two $R^1$ groups within one $P^1$ or $P^2$ ligand constitute an optionally substituted bicycloalkyl.

31. The method of clause 32 wherein the catalyst is of formula (I):

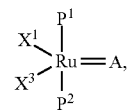

wherein:

$P^1$ and $P^2$ are as defined in clause 30;

$X^1$ and $X^2$ are anionic ligands, which may be the same or different; and

A is an alkylidene group.

32. The method of clause 30 or clause 31 wherein each $R^1$ is independently a branched $C_{5-10}$ alkyl, $C_{5-10}$ cycloalkyl, $C_{5-10}$ alkoxy or $C_{5-10}$ cycloalkoxy group optionally substituted once with a sulfonate, phosphate carboxylate, quaternary ammonium or PEG-containing group.

33. The method of any one of clauses 30 to 32 wherein each $R^1$ is unsubstituted and independently a branched $C_{5-10}$ alkyl, $C_{5-10}$ cycloalkyl, branched $C_{5-10}$ alkoxy or $C_{5-10}$ cycloalkoxy group.

34. The method of clause 32 or clause 33 wherein each $R^1$ is independently a $C_{5-10}$ cycloalkyl group.

35. The method of any one of clauses 30 to 34 wherein at least one of ligands $P^1$ and $P^2$ is tricyclohexylphosphine.

36. The method of any one of clauses 30 to 35 wherein both ligands $P^1$ and $P^2$ are the same.

37. The method of any one of clauses 30 to 36 wherein the alkylidene group is a moiety of formula $=CR^yR^z$ and in which one of $R^y$ and $R^z$ may be hydrogen and either or both of $R^y$ and $R^z$ may be alkyl, alkenyl, alkynyl, aryl carboxyalkyl, alkoxy, alkenyloxy, alkynyloxy or alkoxycarbonyl, or $R^y$ and $R^z$ together form a saturated, unsaturated or aromatic cyclic or bicyclic moiety.

38. The method of clause 37 wherein $R^y$ is hydrogen, alkyl or aryl and $R^z$ is alkyl, alkenyl or aryl 39. The method of clause 37 wherein the alkylidene group is optionally substituted indenylidene.

40. The method of clause 39 wherein the alkylidene group is a phenyl-substituted indenylidene.

41. The method of clause 39 wherein the alkylidene group is 3-phenyl-1H-inden-1-ylidene.

42. The method of clause 41 wherein the catalyst is a dihalo(3-phenyl-1H-inden-1-ylidene)bis(tricyclohexylphosphine) ruthenium (II).

43. The method of clause 42 wherein the catalyst is a dichloro(3-phenyl-1H-inden-1-ylidene)bis(tricyclohexylphosphine) ruthenium (II).

44. The method of clause 37 wherein the alkylidene group is phenylidene.

45. The method of any one preceding clause wherein the diene is a diene consisting only of carbon and hydrogen atoms.

46. The method of clause 45 wherein the diene is a cyclic diene.

47. The method of clause 46, wherein the diene is 1,4-cyclohexadiene.

48. Use of a diene to promote an ethenolysis reaction conducted on a monoalkene.

49. The use of clause 48, wherein the use comprises a method of any one of clauses 1 to 47.

50. An alkene obtained or obtainable by a method defined in any one of clauses 1 to 47 or according to the use defined in clause 48 or clause 49.

The invention is further illustrated by the following non-limiting examples below:

As homogeneous metathesis catalysts are very sensitive towards impurities, cardanol (2) was purified prior to use. Following a known literature procedure anacardic acid (1) was isolated from CNSL and heated to 200° C. for 3 h.[3] After decarboxylation a brown viscous liquid remained, which was further purified by distillation at 230° C. under vacuum. 2 could be isolated as a pale yellow, slightly viscous liquid, which was stored under nitrogen atmosphere. GC-MS and $^1$H-NMR analysis showed almost pure cardanol (2), which contained 37.9% monoene 2b, 19.9% diene 2c, 37.5% triene 2d and 4.7% saturated cardanol 2a. Separation of these various unsaturated compounds via column chromatography proved difficult, so the cardanol mixture 2 was used without further purification.

Cardanol Ethenolysis

In a first set of experiments various homogeneous metathesis catalysts were tested in the ethenolysis of cardanol 2. During ethenolysis, a propagating methylidene species is formed, which reacts with cardanol (2) to release a terminal alkene 3-nonenyl phenol (4) in the case of mono-unsaturated cardanol 2b.[15] Most alkene metathesis catalysts are unstable as methylidene complexes and undergo rapid decomposition, which affects the selectivity and productivity of the ethenolysis reaction.[14] Therefore, $1^{st}$ generation type, $2^{nd}$ generation type and Grubbs-Hoveyda type catalysts were screened in order to identify a suitable catalyst system for the selective ethenolysis of cardanol:

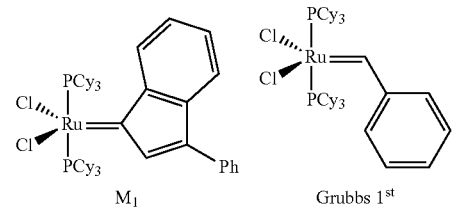

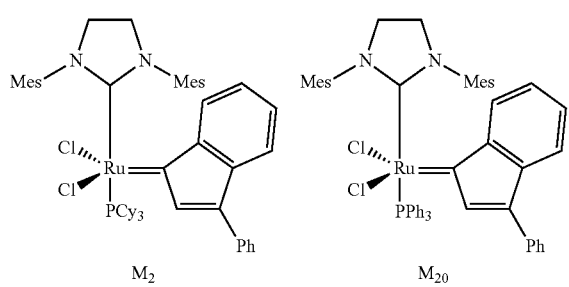

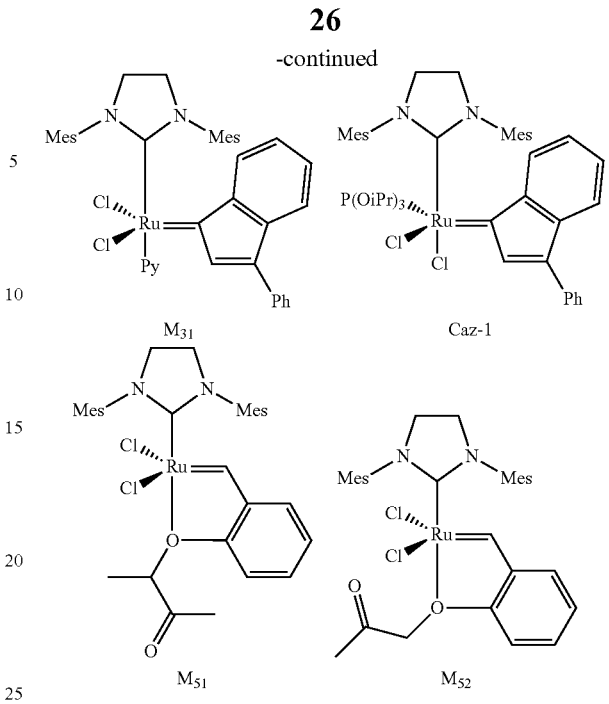

Owing to their varying stability and activity the performance of the metathesis catalyst was investigated at various temperatures. Beside the expected ethenolysis products, 3-non-8-enylphenol (4) and 1-octene (6), which are formed by cross-metathesis of ethene with 2 containing only 1 double bond, 1,4-cyclohexadiene (7), 3-dodecadienylphenol (5) and various isomeric ethenolysis products were also observed in the reaction mixture:

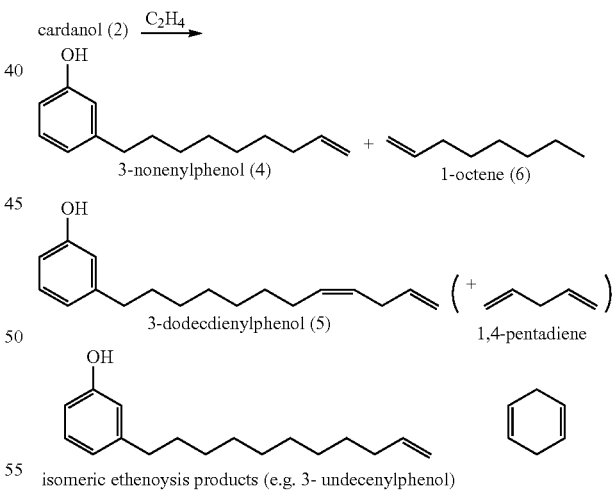

The isomeric ethenolysis products are mainly formed via isomerisation of the monounsaturated cardanol 2b, followed by cross-metathesis with ethene. Ethenolysis at the unsaturated $C_{11}$-position of the diene 2c and triene 2d lead to the side-product 3-dodeca-8,11-dienylphenol (5). However, owing to their volatility the corresponding side-products 1,4-pentadiene and 1-pentene were not observed.

Reacting 2 with $M_1$ at room temperature gives almost exclusive conversion (43%) to 3-non-8-enylphenol (4, 81% selectivity) and its isomers together with 1,4-cyclohexadiene (7), the remaining unreacted cardanol (2) contains no 2d (absence of peaks with m/e 298, [M]+; Entry 2, Table 1). This reaction shows that 7 can be formed by direct internal self-metathesis of the triene (2d) to 7 and 4. However, 7 might also be formed from the ethenolysis of the triene (2d) at the unsaturated $C_{8,9}$-position, giving 3-nonenylphenol (4) and 1,4,7-octatriene, followed by the internal self-metathesis of the 1,4,7-triene to ethene and 7.

Because of the high percentage of triene 2d in the starting material, the amount of 1,4-cyclohexadiene (7) is significant and almost in the same range as 1-octene (6).

As some of the side-products such as the diene (7) and the linear alkenes with an alkyl chain <C7 are volatile, it was not possible reliably to determine their exact amounts via GC analysis. Therefore, we analysed the distribution of the corresponding alkenylphenols.

The results in Table 1 below show that the conversion and the selectivity in the ethenolysis of cardanol (2) strongly depend on the metathesis catalyst and the reaction temperature. Quite unexpectedly the best results were obtained with the $M_1$ and the Grubbs $1^{st}$ generation catalysts (Entries 1-6, Table 1). Both catalytic systems exhibited an excellent performance in the ethenolysis with yields and selectivities >90% towards the desired product, 4, (catalyst loading. 0.05 mol %). Only a minor influence of the temperature on the activity was observed. And changing to the more environmentally acceptable solvent, toluene from $CH_2Cl_2$ was only slightly detrimental. (Table 1, Entry 4) Furthermore, the metathesis reaction of cardanol (2) with $M_1$, but with no ethene present showed that 2 can undergo self-metathesis to form 1,4-cyclohexadiene (7) and the desired 3-nonenylphenol (4) (Entry 2, Table 1). Only the tri-unsaturated cardanol 2d is able to react to give 4 and 7 via self-metathesis, hence the conversion of the reaction (43%) is similar to the amount of tri-unsaturated cardanol 2d in the substrate mixture (37.5%; the slight difference is within the experimental error of the GC measurements). This result indicates that metathesis of 2 with $M_1$ and ethene probably proceeds by a combination of self-metathesis (for the triene 2d) and ethenolysis (for the monoene 2b and diene 2c).

The N-heterocyclic carbene (NHC) bearing $2^{nd}$ generation type[16-19] catalysts $M_2$, $M_{20}$, $M_{31}$ and Caz-1 (Entries 7-18, Table 1) were generally less active and selective in the ethenolysis of cardanol mixture, 2, compared to the Grubbs $1^{st}$ generation catalyst and $M_1$, especially at 20° C. where the conversion and the selectivity were much lower in comparison to the $1^{st}$ generation type catalysts. With increasing temperature the activity and selectivity improved with $M_2$ (Entries 8 and 9, Table 1) and Caz-1 (Entries 17 and 18, Table 1) catalysts giving good performances at 70° C. and 90° C. respectively.

TABLE 1

Conversion and selectivity in the ethenolysis of cardanol (2) using a variety of ruthenium based catalysts.[a]

| Entry | Catalyst | T/° C. | Conv./% | 4/% | 5/% | Isomeric products/% |
|---|---|---|---|---|---|---|
| 1 | $M_1$ | 20 | 95 | 94 | 2 | 4 |
| 2[b] | | 20 | 43 | 81 | 0 | 19 |
| 3 | | 40 | 96 | 93 | 3 | 4 |
| 4 | | 20 | 84 | 87 | 8 | 5 |
| 5 | Grubbs $1^{st}$ | 20 | 90 | 91 | 5 | 4 |
| 6 | | 40 | 91 | 90 | 5 | 5 |
| 7 | $M_2$ | 20 | 57 | 19 | 14 | 67 |
| 8 | | 40 | 61 | 34 | 12 | 54 |
| 9 | | 70 | 84 | 68 | 12 | 20 |
| 10 | $M_{20}$ | 20 | 26 | 43 | 25 | 32 |
| 11 | | 40 | 83 | 54 | 20 | 27 |
| 12 | | 70 | 87 | 49 | 15 | 37 |
| 13 | $M_{31}$ | 20 | 67 | 46 | 24 | 30 |
| 14 | | 40 | 83 | 53 | 19 | 28 |
| 15 | | 70 | 87 | 59 | 22 | 20 |
| 16 | Caz-1 | 40 | 61 | 9 | 12 | 79 |
| 17 | | 70 | 58 | 22 | 14 | 65 |
| 18 | | 90 | 92 | 75 | 12 | 13 |
| 19 | $M_{51}$ | 20 | 82 | 50 | 12 | 38 |
| 20 | | 40 | 93 | 16 | 4 | 80 |
| 21 | | 70 | 90 | 22 | 6 | 72 |
| 22 | $M_{52}$ | 20 | 88 | 23 | 7 | 70 |
| 23 | | 40 | 95 | 24 | 10 | 66 |
| 24 | | 70 | 89 | 22 | 7 | 72 |

[a]2 (0.54 mmol), $C_2H_4$ (8 bar), $CH_2Cl_2$ (1.35 mL), catalyst (0.05 mol %), Analysis via GC using n-tetradecane as internal standard.6 h;
[b]no ethene.

This increased activity with higher reaction temperature could be related to the activation energy of the catalyst since it is known that the latent Caz-1 must isomerise from cis to trans before it becomes active.[20, 21] For the metathesis reaction the catalyst must provide a free coordination site, which is generated via dissociation of a ligand. In contrast to the tricyclohexylphosphine ligands, which readily dissociate at room temperature, methyl- or phosphite ligands are much less labile and need higher temperature to leave the metal center.[20, 21] Nevertheless, even at elevated temperature the activities of the $2^{nd}$ generation type catalysts are lower than those of the $1^{st}$ generation and $M_1$ catalysts. The reduced activity in the ethenolysis is not only visible in the lower conversion, but is also seen in the lower selectivities to product 4.

The Grubbs-Hoveyda type catalysts show even less selectivity in the ethenolysis of cardanol (2). Only in the case of $M_{51}$ is significant selectivity towards the desired 3-nonenylphenol (4) observed at 20° C. (Entry 19, Table 1). Furthermore, the activity and selectivity of $M_{51}$ and $M_{52}$ show only minor dependancies on the reaction temperature (Entries 19-24, Table 1). Both catalytic systems are active at 20° C. and 40° C. respectively, but catalyse mainly the self-metathesis reactions of 2. In comparison to the $2^{nd}$ generation type catalysts, the boomerang-type ligand in $M_{51}$ and $M_{52}$ can easily dissociate to generate a free coordination site. It has been proposed that the ligand remains close to the metal centre and re-coordinates after the catalytic cycle to stabilise the complex,[15] but this recoordination has been disputed.[22] In any case, they are much more active in the conversion of 2 than the $2^{nd}$ generation type catalysts. In general, NHC-based ruthenium catalyst are known to be more active and stable than the first-generation catalyst but are significantly less selective in ethenolysis, as they tend to promote self-metathesis.[14]

Forman et al. showed that the performance of certain alkene metathesis reactions by 1$^{st}$ generation catalysts could be enhanced by the addition of phenols.[23] In the presence of phenol only small quantities of undesired by-products were detected and the activity of the catalytic system was significantly increased. We reasoned, therefore, that the phenol present in cardanol (2) might be responsible for the excellent activity and selectivity provided by 1$^{st}$ generation and $M_1$ catalysts in the ethenolysis reaction. However, adding phenol to the ethenolysis reaction of 2 with $M_1$ did not improve the catalytic performance. In contrast, we observed no conversion of 2 indicating that, in our case, the addition of phenol inhibits the cross-metathesis of ethene and cardanol (2).

Metathesis of Methyl Protected Cardanol 8

The effect of the phenolic group in cardanol (2) was further tested by etherification of the phenolic —OH with methyl iodine,[24] shown below:

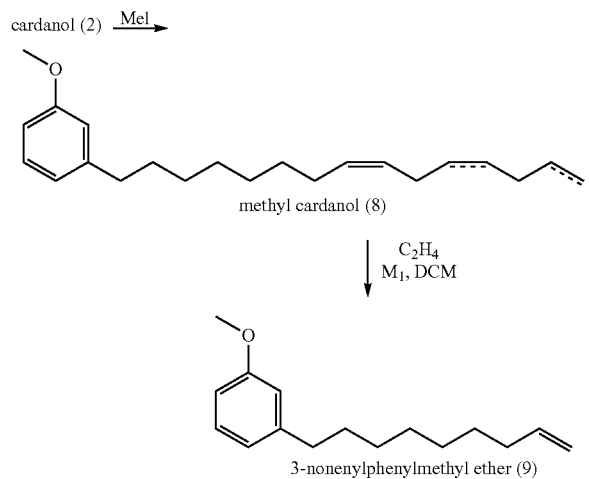

The methyl cardanol (8) was tested in the ethenolysis with $M_1$ under standard reaction conditions. In comparison to the unprotected cardanol 2 the conversion (62.4%) and selectivity towards the desired 3-nonenylphenol methyl ether (9) (84.0%) were both lower than when using cardanol (2) itself as substrate, but higher than when using any of the other metathesis catalysts depicted above with it (i.e. Grubbs 1$^{st}$, $M_2$, $M_{20}$, $M_{31}$, Caz-1, $M_{51}$ and $M_{52}$). The result shows that, although the phenolic structure of 2 may have some beneficial effect on the ethenolysis reaction, there must also be some other reason for the excellent results obtained when using $M_1$ or Grubbs 1$^{st}$ generation catalysts.

Ethenolysis of Mono-Unsaturated Cardanol (2b)

Further information as to the important influences involved in the ethenolysis reactions came from a study of monounsaturated cardanol (2b), which was originally initiate to avoid the formation of 1,4-cyclohexadiene (7) and to maximise the production of 1-octene (6).

Recently, Perdriau et al. reported the selective transfer hydrogenation of a cardanol mixture 2 to mono-unsaturated compound 2b with $RuCl_3 \cdot xH_2O$ in 2-propanol.[25] The transfer-hydrogenation gives access to almost pure 2b, although some double bond isomerisation occurs during the transfer hydrogenation reaction. The mono-unsaturated cardanol 2b was tested in the ethenolysis with $M_1$, Caz-1 and $M_{51}$ under the standard reaction conditions (Table 2).

TABLE 2

Ethenolysis with mono-unsaturated cardanol (2b).[a]

| Entry | Catalyst | T/° C. | Conversion/% | 4/% | Isomeric products/% |
|---|---|---|---|---|---|
| 1 | $M_1$ | 20 | — | — | — |
| 2 | Caz-1 | 70 | 28 | 13 | 87 |
| 3 | $M_{51}$ | 70 | 72 | 9 | 93 |

[a]Conditions as in Table 1

Surprisingly, we could not observe any conversion of the mono-unsaturated cardanol with $M_1$. The catalytic system Caz-1 and $M_{51}$ showed some conversion in the ethenolysis, but in comparison to the unsaturated cardanol mixture 2 the activity and selectivity were also much lower. This observation indicates that the di- and tri-unsaturated cardanol (2c and 2d) are highly beneficial for the ethenolysis of cardanol. Especially in the case of $M_1$ their presence seems to be essential.

A major difference between the mono-unsaturated compound 2b and the natural cardanol mixture 2 is the formation of 1,4-cyclohexadiene (7) during the metathesis reaction of 2d in the latter. To analyse the role of 1,4-cyclohexadiene (7) in the ethenolysis reaction, we added 0.1 equivalent of 1,4-cyclohexadiene (7) to 2b and repeated the metathesis reaction under the standard reaction conditions (cf Table 3):

TABLE 3

Ethenolysis of mono-unsaturated cardanol (2b) with additives.[a]

| Entry | Additive | Conversion/% | 4/% | Isomeric products/% |
|---|---|---|---|---|
| 1 | None | — | — | — |
| 2 | 1,4-cyclohexadiene (7) | 64 | 55 | 46 |
| 3 | 1,4-hexadiene | 63 | 46 | 55 |
| 4 | 1,5-cyclooctadiene | 31 | 47 | 53 |
| 5 | 1,7-octadiene | 69 | 46 | 54 |

[a]Conditions as in Table 1; additive (0.1 equiv)

The addition of 1,4-cyclohexadiene (7) had a major impact on the ethenolysis of monounsaturated cardanol (2b) (compare Entries 1 and 2 in Table 3). In the presence of 1,4-cyclohexadiene 2b (64.4%) underwent metathesis and 3-nonenylphenol (4) was formed (54.5% selectivity). The other products were mainly isomeric metathesis products, which arose from double bond positional isomers of the monoene 2b that were formed during the transfer hydrogenation reaction.[25] Since without diene 7 we observed no reaction, these results indicate that 7 has a positive effect on the $M_1$ catalyst during the ethenolysis reaction. We also tested other dienes as additives in the metathesis of mono-unsaturated cardanol 2b (Table 3, Entries 3-5). With all three additives we could see an improved activity of the $M_1$ catalyst in the ethenolysis. The effect of 1,5-cyclooctadiene on the catalytic activity was less pronounced, giving a lower conversion (31.2%, Entry 4, Table 1). This is possibly because 1,5-cyclooctadiene can coordinate through both double bonds to the metal centre and hence may block coordination of the double bond in 2. However, it still gives better catalysis than is obtained in its absence. These results suggest that the formation of 1,4-cyclohexadiene (7) in the ethenolysis of the natural cardanol mixture 2 is very important for the stabilisation of $M_1$ and its activity in the metathesis reaction of cardanol (2) with ethene.

Caz-1 and $M_{51}$ were also tested in the ethenolysis of mono-unsaturated cardanol (2b) with 1,4-cyclohexadiene (7) as additive, see Table 4:

TABLE 4

Ethenolysis of mono-unsaturated cardanol 2b with different catalysts with or without 1,4-cyclohexadiene (7).[a]

| Entry | Catalyst | Conversion/% | 4/% | Isomeric products/% |
|---|---|---|---|---|
| 1[b] | Caz-1 | 28 | 13 | 87 |
| 2[b] | Caz-1 + 1,4-CHD | 78 | 11 | 90 |
| 3[c] | M51 | 72 | 7 | 93 |
| 4[c] | M51 + 1,4-CHD | 64 | 2 | 98 |

[a]Conditions as in Table 1;
[b]70° C.;
[c]40° C.

In the case of Caz-1 the addition of 7 leads to an increase in conversion of 2b up to 80%. However, mainly isomeric products of cardanol (2) were formed and only 10.5% of the desired 3-nonenylphenol (4) was detected. With $M_{51}$ no enhancement of the catalytic performance was observed.

Owing to its positive effect in the ethenolysis of mono-unsaturated cardanol 2b with $M_1$, we also analysed the influence of 1,4-cyclohexadiene (7) in the ethenolysis of 2b protected via etherification with methyl iodide (see Table 5).

TABLE 5

Ethenolysis of methyl-protected mono-unsaturated cardanol 8b with different catalyts and 7 as additive.[a]

| Entry | Catalyst | Conversion/% | 4/% | Isomeric products/% |
|---|---|---|---|---|
| 1[b] | $M_1$ | 53 | 50 | 50 |
| 2[b] | $M_1$ + 1,4-CHD | 56 | 53 | 37 |
| 3[c] | Caz-1 | 71 | 6 | 94 |
| 4[c] | Caz-1 + 1,4-CHD | 80 | 8 | 92 |
| 5[d] | $M_{51}$ | 77 | 2 | 98-5 |
| 6[d] | $M_{51}$ + 1,4-CHD | 86 | 3 | 97 |

[a]Conditions as in Table 1;
[b]rt;
[c]70° C.;
[d]40° C.

Ethenolysis of Oleate 10 and Linoleate Esters 12

The highly beneficial combination of $M_1$+1,4-cyclohexadiene (7) was also tested in the ethenolysis of oleate and linolenate based substrates:

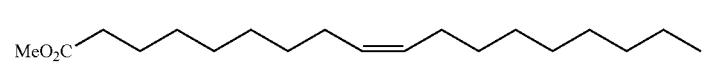

10

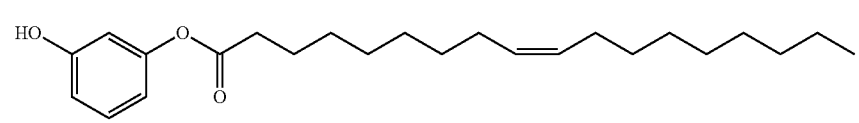

11

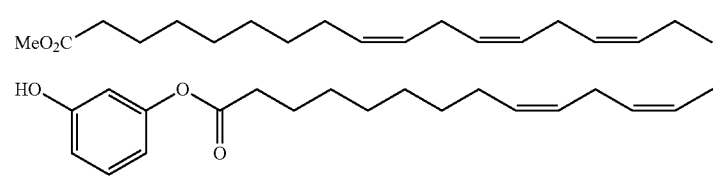

12

13

These results indicate that the effect of the diene (7) strongly depends on the metal catalyst employed.

The results in Table 6 show that 7 also has a positive effect in the ethenolysis of methyl oleate (10) (Entries 1 and 2, Table 6), increasing the conversion of 10 to the ethenolysis product methyl 9-decenoate by more than 25% However, $M_1$ is inactive for the metathesis of methyl linolenate (12) in the presence or absence of the diene 7 (Entries 5 and 6, Table 6).

TABLE 6

Ethenolysis of different olefinic substrates (10-13) with $M_1$.[a]

| Entry | Substrate | Conversion/% | Selectivity/% |
|---|---|---|---|
| 1 | 10 | 47 | 89 |
| 2 | 10 + 1,4-CHD | 76 | 94 |
| 3 | 11 | 7 | 62 |
| 4 | 11 + 1,4-CHD | 13 | 57 |
| 5 | 12 | — | — |
| 6 | 12 + 1,4-CHD | — | — |
| 7 | 13 | 36 | 75 |
| 8 | 13 + 1,4-CHD | 5 | — |

[a]Conditions as in Table 1.

To confirm that it was not the phenol in cardanol (2) that was allowing the excellent results obtained in ethenolysis reactions using $M_1$, we synthesised the resorcinol esters of oleic (11) and linolenic (13) acids. Introducing the phenol moiety into the oleic ester dramatically reduced the conversion and the selectivity towards the desired non-8-enoic acid ester (Entry 3, Table 6), a result that was hardly improved by adding 7 (Entry 4, Table 6). In the case of linolenate, there was some small improvement as a result of using the resorcinol ester 13 (Entry 7, Table 6), but this was nullified by adding the diene (7) (Entry 8, Table 6). Overall, the results of these ethenolysis reactions with oleate and linoleate esters 10-13 confirm that the phenol moiety is at best neutral or inhibiting to the reactions, but that 1,4-cyclohexadiene (7) can provide a positive effect, even counteracting any negative effect of the phenyl group.

Ethenolysis of Anacardic Acid (1) and its Derivatives

Anacardic acid (1) can also be obtained directly from CSNL, but using fewer steps than are required for the isolation of cardanol (2). It can potentially give the desired 3-nonenylphenol (4) by ethenolysis followed by decarboxylation. Preliminary studies on the ethenolysis of anacardic acid itself using $M_1$ catalyst (conditions reported in Table 1, entry 1) showed no evidence for reaction. We therefore methylated anacardic acid at both the phenolic and acidic positions. The ester 14 could then be purified by distillation without decarboxylation of the carboxyl group. Because of the lower activity of $M_1$ in the ethenolysis of methyl cardanol (8, see above) we directly investigated a range of Grubbs-Hoveyda type catalysts:

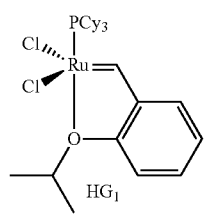

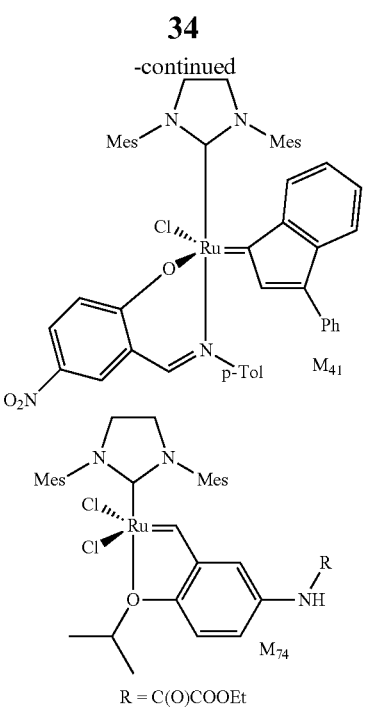

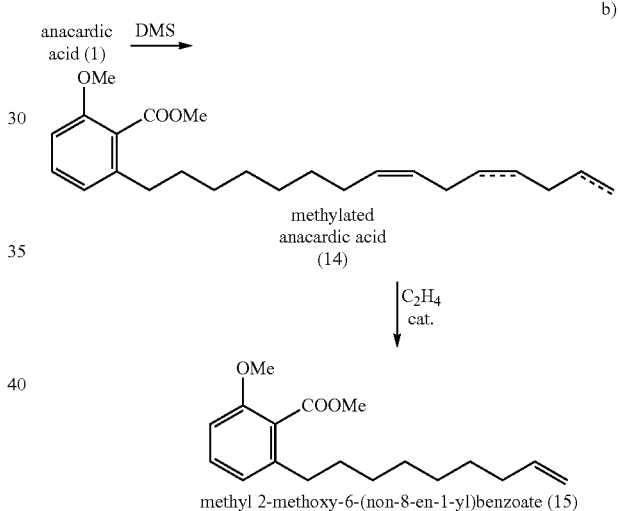

a) Catalyst used for the ethenolysis of methylated anacardic acid (14);
b) Synthesis and ethenolysis of 14. DMS = dimethylsulfate.

which showed high efficiency in our previously investigated isomerising ethenolysis of methyl oleate[26] and of alkenyl benzenes[27]:

The results of these studies, collected in Table 7, show that of all the catalysts tested only the phosphine containing catalyst, $HG_1$ shows high activity and selectivity at 25° C. and a catalyst loading of 1 mol % over 16 h (Entry 1, Table 7).

TABLE 7

Ethenolysis of dimethylated anacardic acid 14.[a]

| Entry | Metathesis catalyst | T/° C. | Conversion/% | Selectivity/% |
|---|---|---|---|---|
| 1 | $HG_1$ | 25 | 93 | 93 |
| 2 | $M_{31}$ | " | 17 | 13 |
| 3 | $M_{41}$ | " | 30 | 18 |
| 4 | $M_{51}$ | " | 96 | 36 |

TABLE 7-continued

Ethenolysis of dimethylated anacardic acid 14.[a]

| Entry | Metathesis catalyst | T/° C. | Conversion/% | Selectivity/% |
|---|---|---|---|---|
| 5 | $M_{74}$ | " | 90 | 37 |
| 6[b] | $HG_1$ | 60 | 74 | 57 |
| 7[b] | $M_{51}$ | " | 88 | 16 |
| 8[b] | $M_{31}$ | " | 56 | 11 |
| 9[b] | $M_{41}$ | " | 44 | 19 |
| 10[b] | $M_{74}$ | " | 93 | 7 |
| 11[c,d] | $HG_1$ | 25 | 98 | 92 |
| 12[c,e] | " | " | 92 | 93 |
| 13[c,f] | " | " | 78 | 93 |

[a]Conditions: 14 (0.25 mmol), cat. (1 mol %), $CH_2Cl_2$ (1 mL), 16 h;
[a]yields were determined using n-dodecane as internal standard;
[b]THF (1 mL);
[c]reaction time 6 h;
[d]cat. (0.5 mol %);
[e]cat. (0.1 mol %);
[f]cat. (0.05 mol %).

Amongst the other catalysts (Entries 3-8, Table 7), only $M_{51}$ and $M_{74}$ show good activity (Entries 4 and 5, Table 7), but their selectivity towards the desired product 15 bearing an 8-nonenyl substituent is low. There is little or no improvement for any of the catalysts at higher temperature (Entries 6-10, Table 7) but $HG_1$ is adversely affected. At 25° C. $HG_1$ performs well even at lower catalysts loading (Entries 11-13, Table 7) with a slight drop in activity but with the high selectivity being retained.

Test for Oestrogenicity

Owing to their excellent properties, ethoxylated alkylphenols (APEs) are widely used in various applications, for example as emulsifiers, detergents or surfactants in household products. Nevertheless, they are being replaced by ethoxylated alcohols because of environmental concerns. One of the most important APEs has been banned in Europe because its precursor, 4-nonylphenol is an endocrine disrupter,[12, 13] for example, it has been shown to induce testes-ova, and intersex condition, in the post-hatching stages of development of male Japanese Medaka fish.[28] The form of 4-nonylphenol used has a variety of differently branched $C_9$ chains in the 4 position of the phenol and its endocrine disrupting properties have been attributed to its ability to mimic the structure of oestradiol:

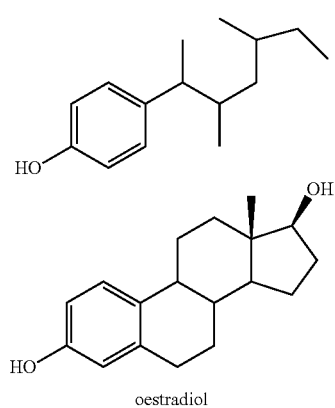

oestradiol

We reasoned that 3-nonylphenol might be less endocrine disrupting than 4-nonylphenol since it has a linear $C_9$ chain in the 3 position and should not so readily mimic oestradiol.

Some of us have shown[13] that the oestrogenicity of alkyl phenols increases in the order 2<3<4 alkyl substitution on the ring and primary~secondary<tertiary. Linear 4-nonyl phenol has been studied before[13] and is known to show lower oestrogenicity than the commercial 4-nonylphenol with mixed alkyl chains, but 3-nonyl phenol has not been examined.

In order to test our hypothesis that 3-nonylphenol might show less oestrogenicity than either the linear or the 4-nonylphenol, we have carried out a yeast oestrogen screen (YES) assay which is specific for oestradiol mimics. For comparison, we also tested oestradiol, 4-nonylphenol with mixed $C_9$ chains (4-NP), 4-nonylphenol with a linear chain (4-n-NP), 3-nonylphenol (3-NP) prepared in this study by hydrogenation of 3-nonenylphenol, cardanol and crude cashew nut shell liquid.

FIG. 1 shows the oestrogenic response of 3-n-NP and 4-n-NP tested over a concentration range of $1 \times 10^{-3}$ mol $dm^{-3}$ to $5 \times 10^{-7}$ mol $dm^{-3}$. Consistent with previous reports,[13] moving the linear alky group from the 4- to the 3-position resulted in a 10-fold reduction in oestrogenic activity to produce a full dose response curve with a potency approximately $1.5 \times 10^6$ and 300-fold less than 17 β-oestradiol and 4-NP (mixed isomers), respectively. The initial sample of 3-NP, which had been obtained using Pd/C as the hydrogenation catalyst contained small amounts of ring hydrogenated product as a result of over hydrogenation. A second sample was prepared using [$RhCl(PPh_3)_3$] as the hydrogenation catalyst. This sample which did not contain any ring hydrogenation products exhibited a 2-fold increase in oestrogenicity, which still 150 times lower than that of 4-NP mixed isomers. The reason for the difference between the pure and contaminated samples is unknown, but may suggest that impurities containing saturated rings in the sample may have contributed to the loss of oestrogenicity, and/or that the ring hydrogenated products are less oestrogenic.

Figure 2:
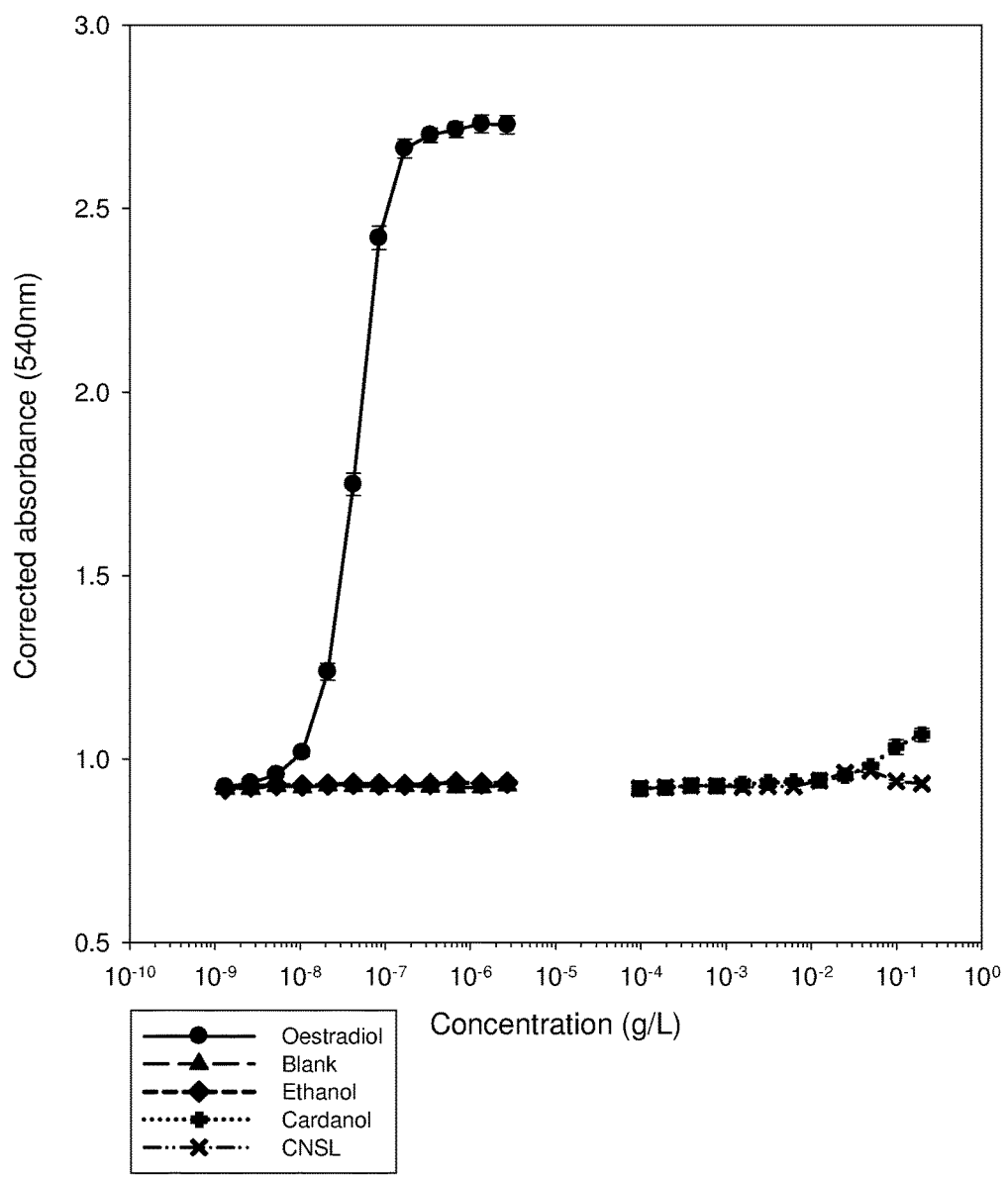
FIG. 2 shows oestrogen response curves for cardanol and CNSL compared with oestrodiol using a YES assay.

Cardanol produced a very weak oestrogenic response at the highest concentrations tested whereas the cashew nut shell liquid was not oestrogenic in the YES assay when tested over the same concentration range (FIG. 2).

Experimental

All reagents were purchased from Sigma-Aldrich and used as received unless otherwise stated. 17 β-oestradiol (98% pure) was purchased from Sigma Chemical Company Ltd. (Dorset, UK) and ethanol (>99.7%) was purchased from Hayman Speciality Products (Essex, UK). All other solvents were purchased from Sigma-Aldrich and were distilled under $N_2$ using the appropriate drying reagent.[29] CNSL was extracted from shells collected from Naliendele in Mtwara, Tanzania. Anacardic acid was obtained from the oil by a literature method[3] and cardanol (2) from the anacardic acid (1) as previously published.[10] The cardanol (2) was vacuum dried before it was subjected to ethenolysis reactions.

Instrumentation

All weighing manipulations of air- and moisture-sensitive chemicals were carried out in the glove box of model type FF100 Recirc 13649 series, where the port was evacuated for 30 minutes and flooded with nitrogen gas for 3 cycles.

All reactions which used air sensitive chemicals were carried out under nitrogen atmosphere using standard Schlenk line and catheter techniques.

GC-MS analyses were carried out using a Hewlett-Packard 6890 series gas chromatograph instrument equipped with a flame ionization detector for quantitative analysis and a Hewlett-Packard 5973 series mass selective detector fitted with hp1 film for mass spectral identification of products. Helium was used as the carrier gas with initial flow of 1 mL/min. The $^1$H NMR and $^{13}$C NMR spectra were recorded on a Bruker AM 400 NMR spectrometer at 400 and 100 MHz or a Bruker AM 300 spectrometer at 300 and 75 MHz, respectively. Samples were dissolved in deuterated solvents which were referenced internally relative to tetramethylsilane (TMS) at δ=0 ppm. Chemical shifts, δ, are reported in ppm relative to TMS. All 13C NMR spectra were proton-decoupled.

Analysis of Cardanol (2).

Cardanol was analysed via GC and NMR. $^1$H NMR (300 MHz, $CDCl_3$): δ 0.93-1.00 (m, 1.9H, $CH_3/CH_2$), 1.33-1.45 (m, 12.4H, $CH_2$), 2.05-2.14 (m, 2.1H, $CH_2$), 2.57-2.62 (m, 3.1H, $CH_2$), 2.83-2.92 (m, 1.9H, $CH_2$), 5.03-5.16 (m, 0.8H, CH), 5.33-5.56 (m, 4.0H, CH), 5.82-5.95 (m, 0.4H, CH), 6.70-7.22 (m, 4H, Ar—H) ppm. $^{13}$C (75 MHz, $CDCl_3$): 14.3, 14.6 ($CH_3$), 32.1, 23.3, 26.0, 26.1, 27.6, 27.7, 29.4, 29.7, 29.8, 29.9, 30.1, 30.1, 30.2, 31.7, 32.0, 32.2, 36.3 ($CH_2$). 127.3, 128.0, 128.4, 128.6 129.7, 129.8 (CH), 130.4, 130.6, 130.8, 137.3, 145.3, 155.8 (Ar—C) ppm. The integration of the $^1$H NMR-signals did not result in even numbers, as cardanol is a mixture of compounds of different saturation. Furthermore, more than 21 C-signals can be observed due to the different degrees of saturation. The composition of saturated, mono-, di- and tri-unsaturated cardanol was calculated from integration of the olefinic proton signals the protons adjacent to the double binds and the aromatic protons.

Monounsaturated Cardanol (2d)[25]

$RuCl_3.xH_2O$ (17 mg, 1.1 mmol) was dissolved in 2-propanol (5 ml) and cardanol (0.5 g, 1.66 mmol) was added. The reaction was refluxed for 18 h under an $N_2$ atmosphere. The resulting brown solution was cooled to room temperature and the solvent removed to give a viscous brown oil. The oil was dissolved in $CH_2Cl_2$ (20 ml) and filtered over a 5 $cm^3$ plug of silica to give a yellow oil. Yield: 0.43 g, 1.4 mmol (86%). $^1$H NMR ($CDCl_3$): δ 0.9 (t, 3H, $CH_3$); 1.3 (m, 16H, $CH_2$); 2.0 (m, 4H, $CH_2$—C═C); 2.6 (m, 2H, Ar—$CH_2$—); 5.4 (m, 2H, HC═CH); 6.7-7.2 (m, 4H, Ar) ppm. MS (m/z): 302, 304 (saturated cardanol).

Methyl Protected Monounsaturated Cardanol (8b)[24]

Monounsaturated cardanol (1 g, 3.3 mmol) and potassium carbonate (0.9 g, 6.6 mmol) were suspended in dry acetone (15 ml). Methyl iodide (0.4 ml, 6.6 mmol) was added dropwise and the mixture allowed to reflux for 6 h. The reaction was then allowed to cool to room temperature and the solvent was removed under reduced pressure. The residue was dissolved in ethyl acetate (50 ml). The organic layer was washed with water (3×20 ml), dried over $MgSO_4$, filtered and evaporated to give a yellow oil. The oil was then purified over a silica column using hexane:EtOAc (5:1).

Yield: 55%. $^1$H NMR ($CDCl_3$): δ 0.9 (t, 3H, $CH_3$); 1.3 (m, 16H, $CH_2$); 2.0 (m, 4H, $CH_2$—C═C); 2.6 (m, 2H, Ar—$CH_2$—); 3.8 (s, 3H, $OCH_3$); 5.4 (m, 2H, HC═CH); 6.7-7.2 (m, 4H, Ar) ppm. MS (m/z): 316.

Methyl Linolenate (12).

Oleic acid (0.92 g, 3.5 mmol) and polyethyleneglycol-750 (1.24 g) were dissolved in $CH_2Cl_2$ (5 mL). KOH (0.37 g) was added and, after stirring for 1 h, MeI (0.5 g, 0.22 mL, 3.4 mmol). After stirring for 5 h, during which time a white precipitate formed, water was added followed by NaCl to break the emulsion. The organic phase was collected combined with $CH_2Cl_2$ washings of the aqueous phase (2×5 mL), dried over anhydrous $MgSO_4$ and evaporated to dryness. The product was separated on a silica column using hexane:EtOAc (4:1). GCMS analysis if the product showed it to be contaminated with up to 50% methyl linoleate and traces of methyl oleate. NMR integration also suggests that significant amounts of methyl linoleate are present.

3-Hydroxyphenyl Oleate (11)

Oleic acid (1.6 g, 4.21 mmol) and resorcinol (1.6 g, 14.82 mmol) were dissolved in THF (10 mL). The reaction mixture was cooled to 0° C. and slowly N,N-dicyclohexylcarbodiimide (991 mg, 4.81 mmol) and DMAP (22 mg, 0.18 mmol) were added. The reaction mixture turned turbulent and a white precipitate was formed. The suspension was allowed to warm and was stirred for 85 h at room temperature. Ethyl acetate (25 mL) was added to the mixture and the precipitate was collected by filtration. The filtrate was evaporated and the remaining residue was purified via column chromatography with hexane/EtOAc (4:1) as eluent. Yield: 62%. $^1$H NMR ($CDCl_3$): δ 0.91 (t, $^3J$=6.9 Hz, 3H, $CH_3$), 1.27-1.45 (m, 20H, $CH_2$), 1.75-1.79 (m, 2H, $CH_2$), 2.01-2.07 (m, 4H, $CH_2$), 2.57 (t, $^3J$=7.8 Hz, $CH_2$), 5.36-5.42 (m, 2H, CH), 6.23 (b, 1H, OH), 6.57-6.70 (m, 3H, Ar—H), 7.21 (t, $^3J$=9.0 Hz, 1H, Ar—H) ppm. ESMS (m/z): 373 $[M-H]^+$ 3-Hydroxyphenyl Linolenate (13)

was similarly prepared from linolenic acid (1.2 g, 4.43 mmol), resorcinol (1.6 g, 14.82 mmol), N,N-dicyclohexyl-carbodiimide (998 mg, 4.84 mmol) and DMAP (18.3 mg, 0.15 mmol). Yield: 58%. $^1$H NMR ($CDCl_3$): δ 1.01 (t, $^3J$=7.5 Hz, 3H, $CH_3$), 1.29-1.46 (m, 8H, $CH_2$), 1.73-1.82 (m, 2H, $CH_2$), 2.06-2.16 (m, 4H, $CH_2$), 2.58 (t, $^3J$=7.5 Hz, 2H, $CH_2$), 2.81-2.86 (m, 4H, $CH_2$), 5.31-5.48 (m, 6H, CH), 6.03 (b, 1H, 01-1), 7.56 (b, 1H, Ar—H), 6.66 (t, $^3J$=8.4 Hz, 2H, Ar—H), 7.21 (t, $^3J$=8.4 Hz, 1H, Ar—H) ppm.

3-Nonylphenol[30]

3-nonenylphenol (1 g, 4.6 mmol), in degassed toluene (10 ml), was added to a solution of [$RhCl(PPh_3)_3$] (30 mg, 46 μmol) dissolved in degassed toluene (5 ml) and transferred to a Fischer-Porter bottle which was charged with 6 bar $H_2$ and left to stir overnight at 60° C. The solution filtered over a plug of silica (5 $cm^3$) using $CH_2Cl_2$ (100 ml). The solvent was removed to give a colourless oil. Yield: 0.96 g, 4.4 mmol (96%). $^1$H NMR (CDCl3): δ 0.91 (t, 3H, $CH_3$); 1.3 (m, 12H, $CH_2$); 1.6 (m, 2H, $CH_2CH_2Ar$); 2.6 (m, 2H, $CH_2Ar$); 4.7 (s, 1H, OH); 6.7-7.2 (m, 4H, Ar—H) ppm. $^{13}$C NMR ($CDCl_3$): δ 14.1 ($CH_3$); 22.7 ($CH_2$); 29.2 ($CH_2$); 29.3 ($CH_2$); 29.6 ($CH_2$); 29.8 ($CH_2$); 31.2 ($CH_2$); 31.9 ($CH_2$); 36.0 (Ar—$CH_2$); 113.1 (Ar); 115.6 (Ar); 120.7 (Ar); 129.9 (Ar); 144.8 (qAr); 156.1 (qAr) ppm. MS (m/z): 220.

Hydrogenation of 3-nonenylphenol (4) with Pd/C 3-nonenyphenol (4) ((800 mg, 3.6 mmol) and Pd/C (5 wt %, 39 mg) were placed in an autoclave and dichloromethane (5 ml) was added. The autoclave was pressurized with hydrogen to 10 bar and the suspension was stirred at 40° C. for 6 h. The reaction was then allowed to cool to room temperature and the autoclave was slowly depressurized. The solvent was removed under reduced pressure and the residue was purified via column chromatography with hexane, ethylacetate and diethylether as eluent (7:1:1). Yield 78%. $^1$H NMR (300 MHz, CDCl$_3$): δ 0.91 (t, $^3$J=6.9 Hz, 3H, CH$_3$), 1.19-1.40 (m, 12H, CH$_2$), 1.54-1.67 (m, 2H, CH$_2$), 5.57 (t, $^3$J=8.1 Hz, 2H, CH$_2$), 4.94 (b, 1H, OH), 6.64-6.71 (m, 2H, Ar—H), 6.78 (bd, $^3$J=8.4 Hz, 1H, Ar—H), 7.16 (t, $^3$J=8.4 Hz, 1H, Ar—H) ppm. $^{13}$C (75 MHz, CDCl$_3$): 14.6 (CH$_3$), 23.2 (CH2), 29.8 (CH$_2$), 30.0 (CH$_2$), 30.1 (CH$_2$), 30.2 (CH$_2$), 31.8 (CH$_2$), 32.4 (CH$_2$), 36.3 (CH$_2$), 112.9 (Ar—CH), 115.9 (Ar—CH), 121.5 (Ar—CH), 129.8 (Ar—CH), 145.4 (Ar—C), 155.8 (Ar—C) ppm.

Some completely hydrogenated 3-nonenylphenol to 3-nonylcyclohexanol can be observed in the NMR.

Anacardic Acid Ester (14)[31]

To a stirred solution of anacardic acid (1) (5.00 g, 14.6 mmol) in acetone (30 ml) was added potassium carbonate (8.07 g, 58.4 mmol). Dimethylsulfate (3.72 g, 29.2 mmol) was added in portions for about 10 min at room temperature. After the addition was complete, the solution was heated to reflux for 4 h. The solution was cooled to room temperature and quenched with ammonium chloride (10 ml). Distilled water (30 ml) was added to the reaction mixture, which was then extracted with ethyl acetate (3×30 ml). The organic layer was washed with distilled water (1×10 ml), dried over anhydrous sodium sulfate, and concentrated in vacuo. The crude product was further purified by Kugelrohr distillation (270° C., 1×10$^{-3}$ mbar) to yield 4.31 g (11.6 mmol, 80%) of a bright yellow oil. $^1$H NMR (CDCl$_3$): δ=0.9 (m, 1.77H, CH$_3$); 1.3 (m, 12.07H, CH$_2$); 1.6 (m, 2.23H, CH$_2$); 2.0 (m, 3.02H, CH$_2$—C=C); 2.5 (m, 1.89H, C=C—CH$_2$—C=C); 2.8 (m, 2H, Ar—CH$_2$—); 3.8 (s, 3H, OCH$_3$); 3.9 (s, 3H, 0000H$_3$); 5.0 (m, 0.72H, C=CH$_2$); 5.4 (m, 2H, HC=CH); 5.8 (m, 0.72H, HC=CH$_2$); 6.7-7.2 (m, 4H, Ar) ppm. MS (m/z): 374.

Typical Catalytic Experiments

The catalyst (M$_1$; 2 mg, 2.2 μmop was weighed in the glove box and made up to a standard solution in CH$_2$Cl$_2$ (2 ml), in a Schlenk tube under dinitrogen atmosphere. When required, the additive was added to the standard solution in correct molar amounts (1,4-cyclohexadienene; 27 μl, 55 μmop. The substrate (Monoene; 0.18 ml, 0.55 mmol) was degassed and added to a previously dried and inert Fischer-Porter bottle with magnetic stirrer bar under dinitrogen atmosphere, in CH$_2$Cl$_2$ (1.3 ml). The appropriate amount of catalyst was syringed from the standard solution (0.26 ml) and added to the Fischer-Porter bottle to give the correct substrate concentration (typically 0.35 M substrate, 1:2000 [catalyst:substrate]. The glass bottle was sealed then flushed with ethene five times and pressurised to at 8 bar. The solution was allowed to stir for 6 hrs at the predetermined temperature in the sealed vessel. The reaction was quenched with ethylvinyl ether (0.05 ml) and taken for GC analysis.

Recombinant Yeast Oestrogen Screen

The recombinant hER yeast strain was developed by Glaxo Welcome and details of the yeast oestrogen screen have been described previously (Routledge and Sumpter, 1996).

In brief, yeast cells were transfected with the human oestrogen receptor gene together with expression plasmids; the oestrogen response element and the lac-Z gene encoding the enzyme β-galactosidase. The yeast cells were incubated in medium containing the test chemical and the chromogenic substrate, chlorophenol red-β-D-galactosidase (CPRG), and active ligands induced β-gal expression. The β-galactosidase secreted into the medium causes the yellow CPGR to change into a red product, and this is measurable by absorbance.

Assay Procedure

The medium components were prepared and the standard assay procedure was followed.[32] Chemicals were serially diluted in ethanol and 10 μl volumes were transferred to 96-well flat-bottom plates where the ethanol was allowed to evaporate to dryness. Then, 200 μl medium containing CPRG and yeast (final cell number of 5×10$^5$ cells/ml) was added to each well. Included with every assay was a negative control, ethanol, and a positive control, 17 β-oestradiol (stock solution of 17 β-oestradiol (2×10$^{-7}$ mol dm$^{-3}$) serially diluted in ethanol to achieve final concentrations of 1×10$^{-8}$ mol dm$^{-3}$ to 4.88×10$^{-12}$ mol dm$^{-3}$ in the wells).

The plates were incubated at 32° C. for 3 days, after which absorbance readings were taken at 540 and 620 nm (the second absorbance being a measure of cell density and hence yeast growth). The absorbance values were corrected for cell density using the following equation:

Corrected value=chemical$_{540nm}$−(chemical$_{620nm}$−ethanol blank$_{620nm}$).

All chemicals were tested in duplicate and each YES was carried out at least three times.

CONCLUSION

We showed that M$_1$ is a very active and selective catalyst in the ethenolysis of cardanol to 3-nonenylphenol, an intermediate for potential surfactants. The unexpected high catalytic performance of M$_1$ is due to the side-product 1,4-cyclohexadiene, which is formed during the ethenolysis from the tri-unsaturated component of cardanol. 1,4-cyclohexadiene stabilises the catalytically active species and prevents inhibition by the phenolic group. Absence of 1,4-cyclohexadiene leads to a complete deactivation of M$_1$, as the results of the ethenolysis of mono-unsaturated cardanol showed. The positive impact of 1,4-cyclohexadiene on the catalytic performance was also observed with other substrates such as methyl oleate. It also enables the use of less expensive homogeneous metathesis catalysts in the ethenolysis reaction, one of the most challenging reactions in metathesis.

One application of 3-nonenylphenol is to hydrogenate to 3-nonylphenol as a possible replacement for the banned, on the basis of its endocrine disrupting properties, detergent precursor, 4-nonylphenol. A YES assay shows that 3-nonylphenol prepared by ethenolysis of cardanol is at least 150 times less potent in oestrogencity than the banned substance and some $10^{-6}$ times as oestrogenic as 17 β-oestradiol. Cradnol and cashew nut shell liquid are even less potent showing very little oestrogenicuty in the YES assay. The significance of the loss of oestrogenicity of 3-NP, cardanol and CSNL in terms of their safety in use can only be determined following the outcomes of internationally agreed and validated OECD test methods developed for the identification of endocrine disrupters, including oestrogenicity, (anti)androgenicity and thyroid disruption.

REFERENCES

1. S. H. Azam-Ali and E. C. Judge, *Small scale cashew nut processing* Food and Agriculture Organisation, Rome, 2004.
2. J. H. P. Tyman, *Chem. Soc. Rev.*, 1979, 8, 499.
3. R. Paramashivappa, P. P. Kumar, P. J. Vithayathil and A. S. Rao, *J. Agric. Food Chem.*, 2001, 49, 2548.
4. P. P. Kumar, R. Paramashivappa, P. J. Vithayathil, P. V. S. Rao and A. S. Rao, *J. Agric. Food Chem.*, 2002, 50, 4705.
5. L. P. L. Logrado, C. O. Santos, L. A. S. Romeiro, A. M. Costa, J. R. O. Ferreira, B. C. Cavalcanti, O. Manoel de Moraes, L. V. Costa-Lotufo, C. Pessoa and M. L. dos Santos, *Eur. J. Med. Chem.*, 2010, 45, 3480.
6. Y.-C. Guo, G. Mele, F. Martina, E. Margapoti, G. Vasapollo and W.-J. Xiao, *J. Organomet. Chem.*, 2006, 691, 5383.
7. P. Peungjitton, P. Sangvanich, S. Pornpakakul, A. Petsom and S. Roengsumran, *J. Surfactants, Detergents*, 2009, 12, 85.
8. R. K. Paul and C. K. S. Pillai, *Synthetic Metals*, 2000, 114, 27.
9. G. Vasapollo, G. Mele and R. Del Sole, *Molecules*, 2011, 16, 6871.
10. J. A. Mmongoyo, Q. A. Mgani, S. J. M. Mdachi, P. J. Pogorzelec and D. J. Cole-Hamilton, *Eur. J. Lipid. Sci. Technol.*, 2012, 114, 1183.
11. http://www.icis.com/Articles/2007/08/06/9050162/chemical-profile-1-octene.html.
12. F. L. P. Gabriel, E. J. Routledge, A. Heidlberger, D. Rentsch, K. Guenther, W. Giger, J. P. Sumpter and H.-P. E. Kohler, *Env. Sci. Technol.*, 2008, 42, 6399.
13. E. J. Routledge and J. P. Sumpter, *J. Biol. Chem.*, 1997, 272, 3280.
14. R. M. Thomas, B. K. Keitz, T. M. Champagne and R. H. Grubbs, *J. Am. Chem. Soc.*, 2011, 133, 7490.
15. D. Astruc, *New J. Chem.*, 2005, 29, 42.
16. L. Ackermann, A. Furstner, T. Weskamp, F. J. Kohl and W. A. Herrmann, *Tetrahedron. Lett.*, 1999, 40, 4787.
17. J. K. Huang, E. D. Stevens, S. P. Nolan and J. L. Petersen, *J. Am. Chem. Soc.*, 1999, 121, 2674.
18. M. Scholl, S. Ding, C. W. Lee and R. H. Grubbs, *Org. Lett.*, 1999, 1, 953.
19. M. Scholl, T. M. Trnka, J. P. Morgan and R. H. Grubbs, *Tetrahedron. Lett.*, 1999, 40, 2247.
20. X. Bantreil, A. Poater, C. A. Urbina-Blanco, Y. D. Bidal, L. Falivene, R. A. M. Randall, L. Cavallo, A. M. Z. Slawin and C. S. J. Cazin, *Organometallics*, 2012, 31, 7415.
21. X. Bantreil, T. E. Schmid, R. A. M. Randall, A. M. Z. Slawin and C. S. J. Cazin, *Chem. Commun.*, 2010, 46, 7115.
22. T. Vorfalt, K. J. Wannowius, V. Thiel and H. Plenio, *Chem. Eur. J*, 16, 12312.
23. G. S. Forman, A. E. McConnell, R. P. Tooze, W. J. van Rensburg, W. H. Meyer, M. M. Kirk, C. L. Dwyer and D. W. Serfontein, *Organometallics*, 2005, 24, 4528.
24. R. Holzwarth, R. Bartsch, Z. Cherkaoui and G. Solladie, *Chem. Eur. J*, 2004, 10, 3931.
25. S. Perdriau, S. Harder, H. J. Heeres and J. G. de Vries, *Chem Sus Chem*, 2012, 5, 2427.
26. D. M. Ohlmann, N. Tschauder, J. P. Stockis, P. Goossen, M. Dierker and L. J. Goossen, *J. Am. Chem. Soc.*, 2012, 134, 13716.
27. S. Baader, D. M. Ohlmann and L. J. Goossen, *Chem. Eur. J*, 2013, 19, 9807.
28. M. A. Gray and C. D. Metcalfe, *Env. Tox. Chem.*, 1997, 16, 1082.
29. C. L. L. C. Wilfred and L. F. Armarego, *Purification of Laboratory Chemicals*, Elsevier, North Holland, 2003.
30. J. A. Osborn, F. H. Jardine, J. F. Young and Wilkinso. G, *J. Chem. Soc. A*, 1966, 1711.
31. R. Paramashivappa, P. P. Kumar, P. V. S. Rao and A. S. Rao, *J. Agric. Food Chem.*, 2002, 50, 7709.
32. E. J. Routledge and J. P. Sumpter, *Env. Tox. Chem.*, 1996, 15, 241.

The invention claimed is:

1. A method of ethenolysis of a monoalkene, comprising introducing into a reaction vessel a monoalkene, ethylene and a diene, and subjecting the monoalkene to ethenolysis in the presence of an alkylidene ruthenium alkene metathesis catalyst and the diene, wherein the diene consists only of carbon and hydrogen atoms; and/or is cyclic; and wherein the metathesis catalyst comprises two ligands $P^1$ and $P^2$, which may be the same or different and are of formula $P(R^1)_3$, in which P is a phosphorus atom coordinated to the ruthenium and each $R^1$ is independently an optionally substituted alkyl, cycloalkyl, alkoxy or cycloalkyloxy group; or two $R^1$ groups within one $P^1$ or $P^2$ ligand and the phosphorus atom to which they are attached constitute an optionally substituted bicycloalkane phosphino.

2. The method of claim 1, wherein the monoalkene is optionally esterified selected from a monounsaturated fatty acid and a monounsaturated fatty acid ester.

3. The method of claim 2, wherein the fatty acid comprises from 4 to 28 carbon atoms.

4. The method of claim 2 wherein the fatty acid is selected from the group consisting of oleic acid, sapienic acid, palmitoleic acid, myristoleic acid or erucic acid.

5. The method of claim 4, wherein the fatty acid is oleic acid.

6. The method of claim 2, wherein the fatty acid is esterified.

7. The method of claim 6, wherein the esterified fatty acid is an alkyl ester.

8. The method of claim 2, wherein the monoalkene is methyl oleate.

9. The method of claim 1, wherein a carbon atom of the carbon-carbon double bond of the monoalkene is tethered to an aromatic moiety.

10. The method of claim 9, wherein the aromatic moiety is an aromatic alcohol.

11. The method of claim 9, wherein the method comprises the ethenolysis of cashew nut shell liquid, or one or more components thereof.

12. The method of claim 11 wherein the method comprises the ethenolysis of a monoalkene component of cardanol.

13. The method of claim 11, wherein the method comprises the ethenolysis of

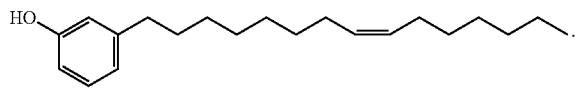 [SMILES: CCCCCC/C=C\CCCCCCCc1cccc(O)c1]

14. The method of claim 11, wherein a product of the ethenolysis reaction is 1-octene.

15. The method of claim 11, wherein a product of the ethenolysis reaction is 3-Non-8-enylphenol.

16. The method of claim 15 further comprising hydrogenating 3-Non-8-enylphenol resulting in 3-nonylphenol and ethoxylating the resultant 3-nonylphenol to provide ethoxy-3-nonylphenol or oligoethoxy-3-nonylphenol, in which the oligoethoxy substituent is of formula —(OCH$_2$CH$_2$)$_n$OH, wherein n is an integer of between 1 and 20.

17. The method of claim 1, wherein the catalyst is of formula (I):

wherein:
P$^1$ and P$^2$ are as defined in claim 1;
X$^1$ and X$^2$ are anionic ligands, which may be the same or different; and
A is an alkylidene group.

18. The method of claim 1, wherein each R$^1$ is independently a C$_{5-10}$ cycloalkyl group.

19. The method of claim 1, wherein at least one of ligands P$^1$ and P$^2$ is tricyclohexylphosphine.

20. The method of claim 1, wherein both ligands P$^1$ and P$^2$ are the same.

21. The method of claim 1, wherein the alkylidene group is a moiety of formula=CR$^y$R$^z$ and (i) one of R$^y$ and R$^z$ is hydrogen and the other of R$^y$ and R$^z$ is selected from the group consisting of alkyl, alkenyl, alkynyl, aryl, carboxyalkyl, alkoxy, alkenyloxy, alkynyloxy and alkoxycarbonyl, or (ii) each of R$^y$ and R$^z$ is selected from the group consisting of alkyl, alkenyl, alkynyl, aryl carboxyalkyl, alkoxy, alkenyloxy, alkynyloxy and alkoxycarbonyl, or (iii) R$^y$ and R$^z$ together form a saturated, unsaturated or aromatic cyclic or bicyclic moiety.

22. The method of claim 21 wherein the alkylidene group is optionally substituted indenylidene.

23. The method of claim 22 wherein the alkylidene group is a phenyl-substituted indenylidene.

24. The method of claim 22 wherein the alkylidene group is 3-phenyl-1H-inden-1-ylidene.

25. The method of claim 24 wherein the catalyst is a dihalo(3-phenyl-1H-inden-1-ylidene)bis(tricyclohexylphosphine) ruthenium (II).

26. The method of claim 25 wherein the catalyst is a dichloro(3-phenyl-1H-inden-1-ylidene)bis(tricyclohexylphosphine) ruthenium (II).

27. The method of claim 21 wherein the alkylidene group is phenylidene.

28. The method of claim 1, wherein the diene is 1,4-cyclohexadiene.

29. The method of claim 1, wherein the diene consists only of carbon and hydrogen atoms, and comprises 4-10 carbon atoms.

30. The method of claim 29, wherein the diene comprises 6-8 carbon atoms.

31. The method of claim 1, wherein the diene is selected from the group consisting of 1,4-hexadiene, 1,5-cyclooctadiene and 1,7-octadiene.

* * * * *